United States Patent
Gaspard et al.

(10) Patent No.: US 12,419,335 B2
(45) Date of Patent: Sep. 23, 2025

(54) READILY DISSOLVABLE STEVIOL GLYCOSIDE COMPOSITIONS

(71) Applicant: CARGILL, INCORPORATED, Wayzata, MN (US)

(72) Inventors: Dan S. Gaspard, Victoria, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 18/335,946

(22) Filed: Jun. 15, 2023

(65) Prior Publication Data

US 2024/0082333 A1 Mar. 14, 2024

Related U.S. Application Data

(63) Continuation of application No. 16/753,869, filed as application No. PCT/US2018/054698 on Oct. 5, 2018, now abandoned.

(60) Provisional application No. 62/676,722, filed on May 25, 2018, provisional application No. 62/569,279, filed on Oct. 6, 2017.

(51) Int. Cl.

| | |
|---|---|
| *A23L 27/30* | (2016.01) |
| *A23F 3/34* | (2006.01) |
| *A23L 2/56* | (2006.01) |
| *A23L 2/60* | (2006.01) |
| *A23L 2/68* | (2006.01) |
| *A23L 5/40* | (2016.01) |
| *A23L 27/00* | (2016.01) |
| *A61K 31/192* | (2006.01) |
| *A61K 31/235* | (2006.01) |
| *A61K 36/28* | (2006.01) |
| *B01D 15/36* | (2006.01) |
| *C07H 15/256* | (2006.01) |
| *C07K 1/16* | (2006.01) |
| *C07K 1/18* | (2006.01) |

(52) U.S. Cl.
CPC ............... *A23L 27/36* (2016.08); *A23F 3/34* (2013.01); *A23L 2/56* (2013.01); *A23L 2/60* (2013.01); *A23L 2/68* (2013.01); *A23L 5/40* (2016.08); *A23L 27/30* (2016.08); *A23L 27/39* (2016.08); *A23L 27/88* (2016.08); *A61K 31/192* (2013.01); *A61K 31/235* (2013.01); *A61K 36/28* (2013.01); *B01D 15/361* (2013.01); *C07H 15/256* (2013.01); *C07K 1/16* (2013.01); *C07K 1/18* (2013.01); *A23V 2002/00* (2013.01); *A23V 2200/15* (2013.01); *A23V 2250/258* (2013.01); *A61K 2236/31* (2013.01); *A61K 2236/39* (2013.01)

(58) Field of Classification Search
CPC .................................. A23L 27/36; A23L 2/60
See application file for complete search history.

(56) References Cited

U.S. PATENT DOCUMENTS

| | | | |
|---|---|---|---|
| 3,916,028 | A | 10/1975 | Lee |
| 3,924,017 | A | 12/1975 | Lee |
| 4,082,858 | A | 4/1978 | Morita |
| 4,312,856 | A | 1/1982 | Korduner |
| 4,495,170 | A | 1/1985 | Beyts |
| 4,710,583 | A | 12/1987 | Chmurny |
| 4,853,237 | A | 8/1989 | Prinkkila |
| 4,906,480 | A | 3/1990 | Kashket |
| 5,336,513 | A | 8/1994 | Riemer |
| 5,681,569 | A | 10/1997 | Kuznicki |
| 5,788,971 | A | 8/1998 | Togasaki |
| 5,888,549 | A | 3/1999 | Buchholz |
| 6,022,576 | A | 2/2000 | Cirigliano |
| 6,337,095 | B1 | 1/2002 | Jain |
| 6,426,112 | B1 | 7/2002 | Boatright |
| 6,475,544 | B1 | 11/2002 | Hiramoto |
| 6,589,588 | B1 | 7/2003 | Wester |
| 6,635,774 | B2 | 10/2003 | Roden |
| 6,900,240 | B2 | 5/2005 | Empie |
| 6,989,171 | B2 | 1/2006 | Portman |
| 7,279,184 | B2 | 10/2007 | Gow |
| 7,291,352 | B2 | 11/2007 | Gow |
| 7,294,353 | B2 | 11/2007 | Gow |
| 7,651,717 | B2 | 1/2010 | Shioya |
| 7,727,565 | B2 | 6/2010 | Jani |
| 7,750,053 | B2 | 7/2010 | Suzuki |
| 7,767,238 | B2 | 8/2010 | Roy |
| 7,838,044 | B2 | 11/2010 | Abelyan |
| 7,879,376 | B2 | 2/2011 | Boghani |
| 7,939,563 | B2 | 5/2011 | Suzuki |
| 8,017,168 | B2 | 9/2011 | Prakash |
| 8,076,491 | B2 | 12/2011 | Karanewsky |

(Continued)

FOREIGN PATENT DOCUMENTS

| | | |
|---|---|---|
| CN | 1085073 A | 4/1994 |
| CN | 1100894 A | 4/1995 |

(Continued)

OTHER PUBLICATIONS

Fu et al., "Production of Chlorogenic Acid and Its Derivatives in Hairy Root Cultures of Stevia rebaudiana," J. of Agric. and Food Chem. 2015, 63, 262-268 (Year: 2015).*

Amazon [online], Aug. 7, 2012 [Retrieval Date: Mar. 28, 2024], Internet: <URL: https://amzn.asia/d/jcWACRC>.

Hariprasad "Cocrystals of Ethenzamide: Study of Structural and Physicochemical Properties", Cryst. Growth Des. 2016; 16: 4473-4481 (Year: 2016).

(Continued)

*Primary Examiner* — Jeffrey P Mornhinweg

(57) ABSTRACT

A readily dissolvable steviol glycoside composition comprising a steviol glycoside and a dissolution enhancer compound in an amount effective to increase dissolution of the steviol glycoside.

19 Claims, No Drawings

(56) References Cited

U.S. PATENT DOCUMENTS

| | | |
|---|---|---|
| 8,088,428 B2 | 1/2012 | Yamane |
| 8,092,795 B2 | 1/2012 | Tsuchiya |
| 8,178,148 B2 | 5/2012 | Fujii |
| 8,197,875 B2 | 6/2012 | Chien |
| 8,241,680 B2 | 8/2012 | Williams |
| 8,337,929 B2 | 12/2012 | Ogura |
| 8,367,137 B2 | 2/2013 | Prakash |
| 8,512,789 B2 | 8/2013 | Prakash |
| 8,524,304 B2 | 9/2013 | Prakash |
| 8,530,527 B2 | 9/2013 | Markosyan |
| 8,703,228 B2 | 4/2014 | Boghani |
| 8,940,350 B2 | 1/2015 | Prakash |
| 8,940,351 B2 | 1/2015 | Prakash |
| 8,956,678 B2 | 2/2015 | Prakash |
| 9,011,956 B2 | 4/2015 | Prakash |
| 9,060,537 B2 | 6/2015 | Mutilangi |
| 9,101,160 B2 | 8/2015 | Prakash |
| 9,101,161 B2 | 8/2015 | Prakash |
| 9,131,719 B2 | 9/2015 | Backes |
| 9,133,229 B2 | 9/2015 | Lee |
| 9,144,251 B2 | 9/2015 | Prakash |
| 9,149,051 B2 | 10/2015 | Prakash |
| 9,358,264 B2 | 6/2016 | Ibarra |
| 9,457,009 B2 | 10/2016 | Guthrie |
| 9,492,379 B2 | 11/2016 | Park |
| 9,510,611 B2 | 12/2016 | Purkayastha |
| 9,629,795 B2 | 4/2017 | Krammer |
| 9,636,373 B1 | 5/2017 | Akao |
| 9,775,822 B2 | 10/2017 | Prasad |
| 9,844,576 B2 | 12/2017 | Brownell |
| 9,848,624 B2 | 12/2017 | Ley |
| 9,889,107 B2 | 2/2018 | Guthrie |
| 9,962,356 B2 | 5/2018 | Prasad |
| 10,188,125 B2 | 1/2019 | Ozato |
| 10,376,521 B2 | 8/2019 | Zaworotko |
| 10,420,744 B2 | 9/2019 | Prasad |
| 10,602,758 B2 | 3/2020 | Dubois |
| 10,624,372 B2 | 4/2020 | Reichelt |
| 10,772,340 B2 | 9/2020 | Hotta |
| 10,780,170 B2 | 9/2020 | Purkayastha |
| 10,798,961 B2 | 10/2020 | Marcq |
| 10,849,339 B2 | 12/2020 | Prakash |
| 10,874,130 B2 | 12/2020 | Kim |
| 10,952,458 B2 | 3/2021 | Purkayastha |
| 10,973,794 B2 | 4/2021 | Forbes |
| 11,000,497 B2 | 5/2021 | Prasad |
| 2001/0051195 A1 | 12/2001 | Miljkovic |
| 2002/0068123 A1 | 6/2002 | Verhagen |
| 2002/0187239 A1 | 12/2002 | Miljkovic |
| 2002/0197386 A1 | 12/2002 | Hiramoto |
| 2003/0003212 A1 | 1/2003 | Chien |
| 2003/0008943 A1 | 1/2003 | Slone |
| 2003/0045473 A1 | 3/2003 | Sarama |
| 2003/0138537 A1 | 7/2003 | Bailey |
| 2003/0172392 A1 | 9/2003 | Mendu |
| 2004/0086619 A1 | 5/2004 | Zhong |
| 2004/0213881 A1 | 10/2004 | Chien |
| 2005/0079232 A1 | 4/2005 | Offord-Cavin |
| 2005/0106215 A1 | 5/2005 | Offord-Cavin |
| 2005/0118293 A1 | 6/2005 | Gow |
| 2005/0220868 A1 | 10/2005 | Lahl |
| 2006/0083838 A1 | 4/2006 | Jackson |
| 2006/0263475 A1 | 11/2006 | Jani |
| 2006/0280835 A1 | 12/2006 | Jani |
| 2006/0286202 A1 | 12/2006 | Boghani |
| 2007/0029258 A1 | 2/2007 | Takeda |
| 2007/0054023 A1 | 3/2007 | Bingley |
| 2007/0082106 A1 | 4/2007 | Lee |
| 2007/0116800 A1 | 5/2007 | Prakash |
| 2007/0116823 A1 | 5/2007 | Prakash |
| 2007/0116828 A1 | 5/2007 | Prakash |
| 2007/0116829 A1 | 5/2007 | Prakash |
| 2007/0116831 A1 | 5/2007 | Prakash et al. |
| 2007/0116838 A1 | 5/2007 | Prakash |
| 2007/0116839 A1 | 5/2007 | Prakash |
| 2007/0128311 A1 | 6/2007 | Prakash |
| 2007/0292582 A1 | 12/2007 | Prakash |
| 2008/0014331 A1 | 1/2008 | Badalov |
| 2008/0063748 A1 | 3/2008 | Massey |
| 2008/0107787 A1 | 5/2008 | Prakash |
| 2008/0226788 A1 | 9/2008 | Chang |
| 2008/0226790 A1 | 9/2008 | Johnson |
| 2008/0261916 A1 | 10/2008 | Jaszberenyi |
| 2008/0286421 A1 | 11/2008 | DeLease |
| 2008/0292764 A1 | 11/2008 | Prakash |
| 2008/0292765 A1 | 11/2008 | Prakash |
| 2008/0292775 A1 | 11/2008 | Prakash |
| 2009/0004360 A1 | 1/2009 | Bingley |
| 2009/0053378 A1 | 2/2009 | Prakash |
| 2010/0028325 A1 | 2/2010 | Rocabayera Bonvila |
| 2010/0099857 A1 | 4/2010 | Evans |
| 2010/0112136 A1 | 5/2010 | Ward |
| 2010/0160224 A1 | 6/2010 | Thomas |
| 2010/0297327 A1 | 11/2010 | Stangle |
| 2010/0330244 A1 | 12/2010 | Nonaka |
| 2011/0033525 A1 | 2/2011 | Liu |
| 2011/0054022 A1 | 3/2011 | Poessel |
| 2011/0091394 A1 | 4/2011 | Abelyan |
| 2011/0104353 A1 | 5/2011 | Lee |
| 2011/0160311 A1 | 6/2011 | Prakash |
| 2011/0189360 A1 | 8/2011 | Yoo |
| 2011/0195161 A1 | 8/2011 | Upreti |
| 2011/0195170 A1 | 8/2011 | Shigemura |
| 2011/0293538 A1 | 12/2011 | Ley |
| 2012/0041078 A1 | 2/2012 | Tachdjian |
| 2012/0058236 A1 | 3/2012 | Fosdick |
| 2012/0064221 A1 | 3/2012 | Given |
| 2012/0076899 A1 | 3/2012 | Evans |
| 2012/0156351 A1 | 6/2012 | Miyazawa |
| 2012/0177602 A1 | 7/2012 | New |
| 2012/0196019 A1 | 8/2012 | Shi |
| 2012/0201935 A1 | 8/2012 | Krohn |
| 2013/0039932 A1 | 2/2013 | Park |
| 2013/0040036 A1 | 2/2013 | Zeller |
| 2013/0071521 A1 | 3/2013 | Lee |
| 2013/0209658 A1 | 8/2013 | Spelman |
| 2013/0251881 A1 | 9/2013 | Mutilangi |
| 2013/0274351 A1 | 10/2013 | Markosyan |
| 2013/0316066 A1 | 11/2013 | Brown |
| 2014/0004215 A1 | 1/2014 | Brownell |
| 2014/0094453 A1 | 4/2014 | Tachdjian |
| 2014/0155359 A1 | 6/2014 | Broze |
| 2014/0171519 A1 | 6/2014 | Prakash |
| 2014/0206634 A1 | 7/2014 | Liu |
| 2014/0295049 A1 | 10/2014 | Ragot |
| 2014/0302180 A1 | 10/2014 | Chapal |
| 2014/0309294 A1 | 10/2014 | Erfurt |
| 2014/0342078 A1 | 11/2014 | Hayes |
| 2015/0017284 A1 | 1/2015 | Prakash |
| 2015/0050410 A1 | 2/2015 | Luo |
| 2015/0125587 A1 | 5/2015 | Asano |
| 2015/0189904 A1 | 7/2015 | Prakash |
| 2015/0223510 A1 | 8/2015 | Lee |
| 2015/0289548 A1 | 10/2015 | Given |
| 2015/0320101 A1 | 11/2015 | Walton |
| 2015/0328179 A1 | 11/2015 | Nakashima |
| 2015/0344456 A1 | 12/2015 | Dull |
| 2015/0366253 A1 | 12/2015 | Shi |
| 2016/0100689 A1 | 4/2016 | Wang |
| 2016/0113316 A1 | 4/2016 | Nachbagauer |
| 2016/0165941 A1 | 6/2016 | Hofmekler |
| 2016/0183574 A1 | 6/2016 | Chen |
| 2016/0213039 A1 | 7/2016 | Kumar |
| 2016/0242452 A1 | 8/2016 | Mutilangi |
| 2016/0309761 A1 | 10/2016 | Brower, III |
| 2016/0316797 A1 | 11/2016 | Piorkowski |
| 2017/0006901 A1 | 1/2017 | Carlson |
| 2017/0055548 A1 | 3/2017 | Chakraborty |
| 2017/0095443 A1 | 4/2017 | Luo |
| 2017/0105432 A1 | 4/2017 | Karanewsky |
| 2017/0119032 A1 | 5/2017 | Patron |
| 2017/0119033 A1 | 5/2017 | Liu |
| 2017/0143012 A1 | 5/2017 | San Miguel |
| 2017/0156374 A1 | 6/2017 | Ackilli |

(56) References Cited

U.S. PATENT DOCUMENTS

| | | |
|---|---|---|
| 2017/0172191 A1 | 6/2017 | Prakash |
| 2017/0183326 A1 | 6/2017 | Kimoto |
| 2017/0273338 A1 | 9/2017 | Lee |
| 2017/0295827 A1 | 10/2017 | Prakash |
| 2017/0303574 A1 | 10/2017 | Luo |
| 2017/0327776 A1 | 11/2017 | Chien et al. |
| 2017/0354175 A1 | 12/2017 | Karanewsky |
| 2017/0362268 A1 | 12/2017 | Carlson |
| 2018/0000133 A1 | 1/2018 | Izumi |
| 2018/0002306 A1 | 1/2018 | Jiang |
| 2018/0086751 A1 | 3/2018 | Karanewsky |
| 2018/0092381 A1 | 4/2018 | Brijwani |
| 2018/0103670 A1 | 4/2018 | Recenti |
| 2018/0168212 A1 | 6/2018 | Markosyan |
| 2018/0177216 A1 | 6/2018 | Markosyan |
| 2018/0263269 A1 | 9/2018 | Prakash |
| 2018/0289042 A1 | 10/2018 | Bell |
| 2018/0296678 A1 | 10/2018 | Prakash |
| 2019/0116835 A1 | 4/2019 | Prakash |
| 2019/0142043 A1 | 5/2019 | Prakash |
| 2019/0175499 A1 | 6/2019 | Zhang |
| 2019/0274985 A1 | 9/2019 | Hotta |
| 2019/0313669 A1 | 10/2019 | Dubois |
| 2020/0009208 A1 | 1/2020 | Hwang |
| 2020/0023021 A1 | 1/2020 | Lewis |
| 2020/0054058 A1 | 2/2020 | Prakash |
| 2020/0085778 A1 | 3/2020 | Yamamoto |
| 2020/0138056 A1 | 5/2020 | Graz |
| 2020/0138765 A1 | 5/2020 | Prasad |
| 2020/0154737 A1 | 5/2020 | Dubois |
| 2020/0196649 A1 | 6/2020 | Mitchell |
| 2020/0197342 A1 | 6/2020 | Russo |
| 2020/0237845 A1 | 7/2020 | Suzuki |
| 2020/0275682 A1 | 9/2020 | Chakraborty |
| 2020/0305483 A1 | 10/2020 | Gan |
| 2020/0345049 A1 | 11/2020 | Galano |
| 2021/0037851 A1 | 2/2021 | Fraser |
| 2021/0051976 A1 | 2/2021 | Fraser |
| 2021/0084949 A1 | 3/2021 | Banavara |
| 2021/0092986 A1 | 4/2021 | Dubois |
| 2021/0128600 A1 | 5/2021 | Rauch |
| 2021/0153536 A1 | 5/2021 | Ozato |
| 2021/0236450 A1 | 8/2021 | Guthrie |
| 2021/0260013 A1 | 8/2021 | Lee |
| 2021/0267243 A1 | 9/2021 | Peterson |

FOREIGN PATENT DOCUMENTS

| | | |
|---|---|---|
| CN | 1144459 A | 3/1997 |
| CN | 1336333 A | 2/2002 |
| CN | 1615838 A | 5/2005 |
| CN | 1651398 A | 8/2005 |
| CN | 1253099 | 4/2006 |
| CN | 100341500 C | 10/2007 |
| CN | 102381974 A | 3/2012 |
| CN | 102771751 A | 11/2012 |
| CN | 102860438 A | 1/2013 |
| CN | 104397785 A | 3/2015 |
| CN | 102924544 B | 4/2015 |
| CN | 103656627 B | 9/2015 |
| CN | 103874411 A | 6/2016 |
| CN | 106138298 A | 11/2016 |
| CN | 107184482 A | 9/2017 |
| CN | 107455718 A | 12/2017 |
| DE | 29603759 U1 | 5/1996 |
| DE | 29808384 U1 | 8/1998 |
| EP | 0730830 A | 9/1996 |
| EP | 1186297 A2 | 3/2002 |
| EP | 1903890 A | 4/2008 |
| EP | 1716757 B1 | 7/2009 |
| EP | 1925208 B1 | 12/2011 |
| EP | 2340719 B1 | 2/2014 |
| EP | 2896301 B1 | 6/2016 |
| EP | 2643007 B1 | 8/2016 |
| EP | 3052074 A1 | 8/2016 |
| EP | 2625962 B1 | 6/2017 |
| EP | 3188604 A1 | 7/2017 |
| EP | 3257507 A1 | 12/2017 |
| EP | 3264919 A1 | 1/2018 |
| EP | 3097790 B1 | 5/2018 |
| EP | 2409696 B1 | 6/2018 |
| EP | 2753188 B1 | 1/2019 |
| EP | 2856883 B1 | 3/2019 |
| EP | 2692243 B1 | 6/2019 |
| EP | 3397072 B1 | 7/2019 |
| EP | 3513663 A1 | 7/2019 |
| EP | 3169166 B1 | 8/2019 |
| EP | 3524062 A2 | 8/2019 |
| EP | 2934181 B1 | 9/2019 |
| EP | 2124647 B2 | 12/2019 |
| EP | 3228195 B1 | 1/2020 |
| EP | 3544445 B1 | 5/2020 |
| FR | 2138067 B1 | 6/1976 |
| GB | 2348104 A | 5/1999 |
| JP | 54147976 A | 11/1979 |
| JP | 63173531 A | 7/1988 |
| JP | 0195739 A | 4/1989 |
| JP | 0427374 A | 1/1992 |
| JP | 04145048 A | 5/1992 |
| JP | 0638723 A | 2/1994 |
| JP | 07123921 A | 5/1995 |
| JP | 07135938 A | 5/1995 |
| JP | 0823939 A | 1/1996 |
| JP | 0994080 A | 4/1997 |
| JP | 09221667 A | 8/1997 |
| JP | 09266767 A | 10/1997 |
| JP | 10179079 A | 7/1998 |
| JP | 10183164 A | 7/1998 |
| JP | 10248501 A | 9/1998 |
| JP | 119189 A | 1/1999 |
| JP | 11299473 A | 11/1999 |
| JP | 2000063827 A | 2/2000 |
| JP | 2000308477 A | 11/2000 |
| JP | 2001321115 A | 11/2001 |
| JP | 2003204756 A | 7/2003 |
| JP | 2002021938 A1 | 1/2004 |
| JP | 2004528050 A | 9/2004 |
| JP | 2006006318 A | 1/2006 |
| JP | 2006104229 A | 4/2006 |
| JP | 2007143528 A | 6/2007 |
| JP | 2009517022 A | 4/2009 |
| JP | 2009523407 A | 6/2009 |
| JP | 2010521166 A | 6/2010 |
| JP | 2011045305 A | 3/2011 |
| JP | 2011168543 A | 9/2011 |
| JP | 2012005483 A | 1/2012 |
| JP | 2012110322 A | 6/2012 |
| JP | 2012240949 A | 12/2012 |
| JP | 2011071179 A | 4/2013 |
| JP | 2015506718 A | 3/2015 |
| JP | 2015511498 A | 4/2015 |
| JP | 2017121221 A | 7/2017 |
| JP | 2017123788 A | 7/2017 |
| JP | 2016084887 A | 9/2017 |
| JP | 2018085964 A | 6/2018 |
| JP | 6710115 B2 | 6/2020 |
| JP | 2019230013 A | 6/2020 |
| JP | 2020-536537 A | 12/2020 |
| JP | 2021-099038 A | 7/2021 |
| KR | 101500485 B1 | 3/2015 |
| PH | 12011000255 A | 7/2011 |
| WO | 1998042209 A1 | 10/1998 |
| WO | 1999030576 W | 6/1999 |
| WO | 2000030464 A1 | 6/2000 |
| WO | 2000062628 A1 | 10/2000 |
| WO | 2000069282 A1 | 11/2000 |
| WO | 2001097624 A1 | 12/2001 |
| WO | 02/21938 A1 | 3/2002 |
| WO | 2002041700 A1 | 5/2002 |
| WO | 02100192 W | 12/2002 |
| WO | 2002096852 A1 | 12/2002 |
| WO | 2007013616 A1 | 2/2007 |
| WO | 2007/061900 A1 | 5/2007 |
| WO | 2007061753 A2 | 5/2007 |

(56) References Cited

FOREIGN PATENT DOCUMENTS

| | | | |
|---|---|---|---|
| WO | 2007061795 A1 | 5/2007 |
| WO | 2007149672 A2 | 12/2007 |
| WO | 2008057965 A2 | 5/2008 |
| WO | 2008093892 A1 | 8/2008 |
| WO | 2008147723 A1 | 12/2008 |
| WO | 2008147725 A1 | 12/2008 |
| WO | 2009012051 A1 | 1/2009 |
| WO | 2010038911 A1 | 4/2010 |
| WO | 2011/071179 A1 | 6/2011 |
| WO | 11094423 W | 8/2011 |
| WO | 2011094423 A1 | 8/2011 |
| WO | 2011105561 A1 | 9/2011 |
| WO | 2011106114 A1 | 9/2011 |
| WO | 2011112892 A1 | 9/2011 |
| WO | 2012083251 A1 | 6/2012 |
| WO | 2012107205 A1 | 8/2012 |
| WO | 2012109506 A1 | 8/2012 |
| WO | 2012166164 A1 | 12/2012 |
| WO | 2013096420 A1 | 6/2013 |
| WO | 2013148177 A1 | 10/2013 |
| WO | 2014104408 A1 | 7/2014 |
| WO | 2014146135 A2 | 9/2014 |
| WO | 2014153000 A1 | 9/2014 |
| WO | 2015023928 A1 | 2/2015 |
| WO | 2015024218 A1 | 2/2015 |
| WO | 2015117011 A1 | 8/2015 |
| WO | 2016036578 A1 | 3/2016 |
| WO | 2016049236 A1 | 3/2016 |
| WO | 2016073251 A1 | 5/2016 |
| WO | 2016/084887 A1 | 6/2016 |
| WO | 16085919 W | 6/2016 |
| WO | 16085924 W | 6/2016 |
| WO | 16086233 W | 6/2016 |
| WO | 2016100689 A1 | 6/2016 |
| WO | 17053980 W | 3/2017 |
| WO | 2017059414 A1 | 4/2017 |
| WO | 2017095932 A1 | 6/2017 |
| WO | 17120480 W | 7/2017 |
| WO | 17189994 W | 11/2017 |
| WO | 2017196933 A1 | 11/2017 |
| WO | 2018013739 A2 | 1/2018 |
| WO | 2018102447 A2 | 6/2018 |
| WO | 2019071182 A1 | 4/2019 |
| WO | 2019071187 A1 | 4/2019 |
| WO | 2019071188 A1 | 4/2019 |
| WO | 2019071220 A1 | 4/2019 |
| WO | 2019071250 A1 | 4/2019 |
| WO | 2019071254 A1 | 4/2019 |
| WO | 19177634 W | 9/2019 |
| WO | 2019177634 A1 | 9/2019 |
| WO | 19222601 W | 11/2019 |
| WO | 2020172276 W | 8/2020 |
| WO | 2020202193 W | 10/2020 |
| WO | 2020210118 A1 | 10/2020 |
| WO | 2020210122 A1 | 10/2020 |
| WO | 2020210160 A2 | 10/2020 |
| WO | 2020237060 A1 | 11/2020 |
| WO | 2021038830 W | 3/2021 |
| WO | 2021038832 W | 3/2021 |
| WO | 2021049864 W | 3/2021 |
| WO | 2021081417 A1 | 4/2021 |
| WO | 2021090989 A1 | 5/2021 |
| WO | 2021091322 A1 | 5/2021 |
| WO | 2021091327 A1 | 5/2021 |
| WO | 2021125070 A1 | 6/2021 |
| WO | 2021132439 W | 7/2021 |

OTHER PUBLICATIONS

Kuminek "Cocrystals to facilitate delivery of poorly soluble compounds beyond-rule-of-5", Adv. Drug Deliv. Rev. 2016; 101: 143-166 (Year: 2016).
Liu Na, et al., "Review on Stevia rebaudiana research abroad in 2015", Sugar Crops of China. 2017, 39(1): 57-64.
Molina-Calle et al., "Development and application of a quantitative method based on LC-QqQ MS/MS for determination of steviol glycosides in Stevia leaves", Talanta 154 (2016) 263-269.
Pimpley et al. "The chemistry of chlorogenic acid from green coffee and its role in attenuation of obesity and diabetes" at https://pubmed.ncbi.nim.nih.gov/32633686. (Year: 2020).
Wang Shaojia, et al., "Progress of functional components in Stevia rebaudiand Bertoni", Science and Technology of Food Industry. 2017, vol. 38, No. 20.
Abeywardena M. Y., et al. (2010) Acute administration of chlorogenic acid reduces blood pressure in the rat. Hypertension 55, 1493 [abstract 002]. DOI:10.1161/HYP.0b013e3181df4279.
Albas C. S., et al (2014) Avaliação da genotoxicidade da Ilex paraguariensis (erva mate) pelo teste do micronúcleo / [Evaluation of the genotoxicity of Ilex paraguariensis (yerba mate) by micronucleus test]. Rev. Bras. Plantas Med. 16, 2, Suppl 1, 345-349 [Portuguese, English abstract]. DOI:10.1590/1983-084X/12_058.
Alkhatib A. and Atcheson, R. (2017) Yerba maté (Ilex paraguariensis) metabolic, satiety, and mood state effects at rest and during prolonged exercise. Nutrients 9, 882 [15pp]. DOI:10.3390/nu9080882.
Ana Covarrubias-Cárdenas et al., "Antioxidant Capacity and UPLX-PDA ESI-MS Phenolic Profile of Stevia rebaudiana Dry Powder Extracts Obtained by Ultrasound Assisted Extraction", Agronomy, vol. 8, No. 9, Aug. 31, 2018 (Aug. 31, 2018), p. 170.
Analysis of the chemical constituents of Stevia rebausiana and its sweetness Reb M structure, Mar. 20, 2012, Journal of Beijing University of Chemical Technology (Natural Science).
Anonymous, "Sparkling Organic Grapefruit Ginger Soda", GNPD 2012, retrieved from www.gnpd.comDatabase accession No. 1790955.
Anonymous, "Stevia production process | Cargill no-calories sweeteners | Cargill", Nov. 4, 2020 (Nov. 4, 2020), Retrieved from the Internet: URL:https://www.cargill.com/food-beverage/emea/stevia-based-sweeteners-production-process.
Anonymous, "Steviol Glycosides Based Table Sweetener", GNPD14 Dec. 2018 (Dec. 14, 2018), Database accession No. 6205393.
Aranda Gonzalez, et al., "Effect of different drying methods on the composition of steviol glycosides in Stevia rebaudiana Bertoni leaves," Int. Agrophys., 2017, 31, 139-144.
Arthur, R., "The stevia story has changed!' PureCircle on the evolution of the natural sweetener," Mar. 11, 2019, Beveragedaily.com,.
Augustijns and Brewster, "Solvent systems and their selection in pharmaceutics and biopharmaceutics," Springer, 2009.
Baeza Gema et al: "Dihydrocaffeic acid, a major microbial metabolite of chlorogenic acids, shows similar protective effect than a yerba mate phenolic extract against oxidative stress in HepG2 cells", Food Research International, Elsevier, Amsterdam, NL, vol. 87, Jun. 17, 2016 (Jun. 17, 2016), pp. 25-33, XP029671195, ISSN: 0963-9969, DOI:10.1016/J.FOODRES.2016.06.011.
Balsan G., et al. (2019) Effect of yerba mate and green tea on paraoxonase and leptin levels in patients affected by overweight or obesity and dyslipidemia: a randomized clinical trial. Nutr. J. 18, 5 [10pp]. DOI: 10.1186/s12937-018-0426-y.
Bariana D. S., et al. (1965) Chlorogenic acid: further evidence for its antigenic and allergenic activity. Nature 207, 1155-1157. DOI:10.1038/2071155a0.
Bartoshuk et al., "Sweet Taste of Water Induced by Artichoke," Dec. 1, 1972, Science, 178 (4064), 988-990.
Berte et al. (2011) J. Agric. Food Chem. 59: 5523-5527. (Year: 2011).
Bidau C. J., et al. (2004) Evaluation of the genotoxicity of aqueous extracts of Ilex paraguariensis St. Hil. (Aquifoliaceae) using the Allium test. Cytologia 69, 109-117. DOI:10.1508/cytologia.69.109.
Boaventura B. C., et al.(2012) Association of mate tea (Ilex paraguariensis) intake and dietary intervention and effects on oxidative stress biomarkers of dyslipidemic subjects. Nutrition 28, 657-664. DOI:10.1016/j.nut.2011.10.017.
Boaventura B. C., et al.(2013) Antioxidant potential of mate tea (Ilex paraguariensis) in type 2 diabetic mellitus and pre-diabetic individuals. J. Funct. Foods 5, 1057-1064. DOI:10.1016/j.jff.2013.03.001.
Boaventura B. C., et al.(2015) Effect of yerba mate (Ilex paraguariensis A. St. Hil.) infusion obtained by freeze concentration technology on

(56) References Cited

OTHER PUBLICATIONS antioxidant status of healthy individuals. LWT Food Sci. Technol. 62, 948-954. DOI:10.1016/j.lwt.2015.02.028.
Boaventura, B. C. B., et al.(2013). Enhancement of bioactive compounds content and antioxidant activity of aqueous extract of mate (*Ilex paraguariensis* A. St. Hil.) through freeze concentration technology. Food Research International, 53, 686e692.
Borges M. C., et al. (2013) The effect of mate tea (*Ilex paraguariensis*) on metabolic and inflammatory parameters in high-fat diet-fed Wistar rats. Int. J. Food Sci. Nutr. 64, 561-569. DOI:10.3109/09637486.2012.759188.
Bortoluzzi M.-C., et al.(2014) Frequency of micronucleus in oral epithelial cells after exposure to mate-tea in healthy humans. Med. Oral Patol. Oral Cir. Bucal. 19, e345-e349. DOI:10.4317/medoral.19570.
Brent, Rhea, "Investigating differences in solubility between crystalline and amorphous forms of pharmaceuticals," AstraZeneca, Mat 2006.
Brittain, Harry, "Thermodynamic vs. kinetic solubility: knowing which is which," American Pharmaceutical Review, 2014.
Carvalho Ribeiro M., et al.(2017) The effects of roasted yerba mate (*Ilex paraguariensis* A. St. Hil.) consumption on glycemia and total serum creatine phosphokinase in patients with traumatic brain injury. J. Funct. Foods 28, 240-245. DOI:10.1016/j.jff.2016.11.
Chang, et al., "Stability studies of stevioside and Rebaudioside A in carbonated beverages," J. Agric. Food Chem., 1983, 31, 409-412.
Chaube S. and Swinyard C. A. (1976) Teratological and toxicological studies of alkaloidal and phenolic compounds from *Solanum tuberosum* L. Toxicol. Appl. Pharmacol. 36, 227-237. DOI:10.1016/0041-008X(76)90002-8.
Chen J., et al. (2018) Dietary chlorogenic acid improves growth performance of weaned pigs through maintaining antioxidant capacity and intestinal digestion and absorption function. J. Anim. Sci. 96, 1108-1118. DOI:10.1093/jas/skx078.
Chiou, et al., "A comparison of crystallisation approaches in spray drying," Jounral of Food Engineering, 2008.
Cilliers, et al., "Total polyphenols in apples and ciders; correlation with chlorogenic acid," Journal of Food Science, vol. 55, No. 5, 1990, pp. 1458-1459.
Clifford, "Chlorogenic acids and other cinnamates—nature, occurance, and dietary burden," Journal of the Science of Food and Agriculture, 79:362-372 (1999).
Coquerel, Gerard, "Crystallization of molecular systems from solution: phase diagrams, supersturation, and other basic concepts," Chem Soc Rev, 2014.
Craig et al., "Performance review of a fast HPLC-UV method for the quantification of chorogenic acids in green coffee bean extracts," Talanta, 154 (2016) 481-485.
Crammer and R I Kan B: II Properties and syntheses of sweetening agents, Chemical Society Reviews, Royal Society of Chemistry, UK, vol. 6, Jan. 1, 1977 (Jan. 1, 1977), pp. 431-465, XP009150156, ISSN: 0306-0012 p. 437, paragraph 2-p. 438, paragraph 1.
Cros et al., "Solvent Extraction of Oil and Chlorogenic Acid from Green Coffffee Part I: Equilibrium Data," Journal of Food Engineering 10 (1989) 1-11.
Cuesta A., et al.(2018) Efecto agudo del consumo de yerba mate (*Ilex paraguariensis*) sobre el ritmo cardíaco en pacientes derivados para estudio Holter [Acute effect of yerba mate (*Ilex paraguariensis*) consumption on heart rhythm in patients referred for Holter study] [epub ahead of print]. Arch. Cardiol. Mex. xxx, Jun. 2, 2018 [1-6] [Spanish, English abstract]. DOI:10.1016/j.acmx.2018.05.004.
De Andrade F., Coehlo de Albuquerque C. A., Maraschin M. and da Silva E. L. (2012) Safety assessment of yerba mate (*Ilex paraguariensis*) dried extract: results of acute and 90 days subchronic toxicity studies in rats and rabbits. Food Chem. Toxicol. 50, 328-334. DOI:10.1016/j.fct.2011.08.028.
De Meneses Fujii et al. (2014) Yerba Mate (*Ilex paraguariensis*) modulates NF-kappaB pathway and AKT expression in the liver of rats fed on a high-fat diet. Int. J. Food Sci. Nutr. 65, 967-976. DOI:10.3109/09637486.2014.945153.

De Morais E. C., et al.(2009) Consumption of yerba mate (*Ilex paraguariensis*) improves serum lipid parameters in healthy dyslipidemic subjects and provides an additional LDL-cholesterol reduction in individuals on statin therapy. J. Agric. Food Chem. 57, 8316-8324. DOI:10.1021/jf901660g.
Deladino L., et al., "Major phenolics in Yerba mate extracts(*Ilex paraguariensis*) and their contribution to the total antioxidant capacity," Food and Nutritional Science, 4, 2013.
Douglass, et al., "Kinetics of dissolution of an amorphous solid," J. Phys. Chem. B, 2018.
DuBois, G. E., et al., "Concentration-Response relationship of sweeteners," ACS Syposium Series, 1991.
Edgar Naegele, "Determination of Chlorogenic Acid in Coffee Products According to DIN 10767," Sep. 1, 2016, Agilent Technology, INC.
Eklund A. (1975) Effect of chlorogenic acid in a casein diet for rats. Nutritional and pathological observations. Nutr. Metab. 18, 258-264. DOI:10.1159/000175603.
Enokuchi Y., et al. (2020) Effects of chlorogenic acids on menopausal symptoms in healthy women: a randomized, placebo-controlled, double-blind, parallel-group trial. Nutrients 12, 3757 [12pp]. DOI:10.3390/nu12123757.
Erk T., et al. (2012) Dose-dependent absorption of chlorogenic acids in the small intestine assessed by coffee consumption in ileostomists. Mol. Nutr. Food Res. 56, 1488-1500. DOI:10.1002/mnfr.201200222.
Folwarczna J., et al. (2012) Effects of caffeic and chlorogenic acids on bone mechanical properties in female rats. Bone 50, Suppl. 1, S158 [abstract PP306]. DOI:10.1016/j.bone.2012.02.495.
Fonseca C. A., et al.(2000) Nontoxic, mutagenic, and clastogenic activities of mate-chimarrao (*Ilex paraguariensis*). J. Environ. Pathol. Toxicol. Oncol. 19, 333-346.
Frank J., et al. (2003) The dietary hydroxycinnamate caffeic acid and its conjugate chlorogenic acid increase vitamin E and cholesterol concentrations in Sprague-Dawley rats. J. Agric. Food Chem. 51, 2526-2531. DOI:10.1021/jf026127k.
Messina D., et al. (2017) Mate tea and lipid profile in overweight women under caloric restriction. Ann Nutr. Metab. 71, 384 [abstract 144-1131]. DOI:10.1159/000480486.
Mikulasova M., et al. (2005) Genotoxic effects of the hydroxycinnamic acid derivatives—caffeic, chlorogenic and cichoric acids. Biologia (Bratisl.) 60, 275-279.
Minuzzi Becker A., et al. (2019) Spray-dried yerba mate extract capsules: clinical evaluation and antioxidant potential in healthy individuals. Plant oods Hum. Nutr. 74, 495-500 [plus supplementary tables]. DOI:10.1007/s11130-019-00764-4.
Miranda D. D. C., et al. (2008) Protective effects of mate tea (*Ilex paraguariensis*) on H2O2-induced DNA damage and DNA repair in mice. Mutagenesis 23, 261-265. DOI:10.1093/mutage/gen011.
Miura et al., "Molecularly imprinted polymer for chlorogenic acid by modified precipitation polymerization and its application to extraction of chlorogenic acid from Eucommia ulmodies leaves," Journal of Pharmaceutical and Biomedical Analysis, 114 (2015) 139-144.
Moeenfard, et al., "Quantification of Caffeoylquinic Acids in Coffee Brews by HPLC-DAD," Journal of Analytical Methods in Chemistry, Dec. 21, 2014.
Monteiro M., et al. (2007) Chlorogenic acid compounds from coffee are differentially absorbed and metabolized in humans. J. Nutr. 137, 2196-2201. DOI:10.1093/jn/137.10.2196.
Moura de Oliveira D., et al. (2017) Bioavailability of chlorogenic acids in rats after acute ingestion of maté tea (*Ilex paraguariensis*) or 5-caffeoylquinic acid. Eur. J Nutr. 56, 2541-2556. DOI:10.1007/s00394-016-1290-1.
Murdande, et al., "Aqueous solubility of crytalline and amorphous drugs: challenges in measurement," Pharmaceutical Development and Technology, 2011.
Murdande, et al., "Solubility Advantage of amorphous pharmaceuticals: I. A thremodynamic analysis," Wiley InterScience, 2009.
Murshedkav, Tooba, "Effect of crystalline to amorphous coversion on solubility of cefuroxime axetil," Univeristy of Rhode Island, 2002.

(56) References Cited

OTHER PUBLICATIONS

Naimi, et al., "Rosemary Extract as a Potential Anti-Hyperglycemic Agent: Current Evidence and Future Perspectives", Sep. 1, 2017, Nutrients; vol. 9, Issue 9, pp. 1-19.
Nakamura S., et al. (2006) [Pharmacokinetics of chlorogenic acids absorbed in human plasma and their metabolites following oral ingestion of coffee drink]. Yakuri To Chiryo [Jpn. Pharmacol. Ther.] 34, 1239-1246 .
Nalte, YK, et al., Solubility Enhancement of Nevirapine by Cocrystallisation Technique. Journal of Pharmacy Research. Aug. 21, 2015, vol. 9, No. 8; pp. 556-561. ISSN:0974-6943.
Naylor L. H., et al. (2021) Acute dose-response effect of coffee-derived chlorogenic acids on the human vasculature in healthy volunteers: a randomized controlled trial. Am. J. Clin. Nutr. 113, 370-379. DOI:10.1093/ajcn/nqaa312.
Nguyen et al., "Facile preparation of water soluble curcuminoids extracted from turmeric (*Curcuma longa* L.) power by using steviol glucosides," Food Chemistry, 2017, 214, 366-373.
Nicoud, et al., "Estimation of the solubility of metastable polymorphs: A critical review," Cryst. Growth Des., 2018.
Notice of Opposition in EP2934181.
Nowacki L. C., et al. (2021) Ilex paraguariensis extract as an alternative to pain medications. Acta Pharm. 71, 383-398. DOI:10.2478/acph-2021-0029.
Ochiai R., et al. (2019) Effect of chlorogenic acids on cognitive function in mild cognitive impairment: a randomized controlled crossover trial. J. Alzheimers Dis. 72, 1209-1216 [plus supplementary tables]. DOI:10.3233/jad-190757.
Ohta et al., "Characterization of Novel Steviol Glycosides from Leaves of Stevia rebaudiana Morita," 2010, J. Appl. Glycosci., 57, 199-209.
Olthof M. R., et al. (2001a) Consumption of high doses of chlorogenic acid, present in coffee, or of black tea increases plasma total homocysteine concentrations in humans. Am. J. Clin. Nutr. 73, 532-538. DOI:10.1093/ajcn/73.3.532.
Olthof M. R., et al. (2001b) Chlorogenic acid and caffeic acid are absorbed in humans. J. Nutr. 131, 66-71. DOI:10.1093/jn/131.1.66.
Olthof M. R., et al. (2003) Chlorogenic acid, quercetin-3-rutinoside and black tea phenols are extensively metabolized in humans. J. Nutr. 133, 1806-1814 [erratum, 133, 2692]. DOI:10.1093/jn/133.6.1806.
Onakpoya I. J., et al. (2015) The effect of chlorogenic acid on blood pressure: a systematic review and meta-analysis of randomized clinical trials. J. Hum. Hypertens. 29, 77-81 [plus supplementary data]. DOI:10.1038/jhh.2014.46.
Park I., et al. (2017) Effects of subacute ingestion of chlorogenic acids on sleep architecture and energy metabolism through activity of the autonomic nervous system: a randomised, placebo-controlled, double-blinded cross-over trial. Br. J. Nutr. 117, 979-984. DOI:10.1017/S0007114517000587.
Pereira Panza V., et al. (2019) Effect of mate tea (*Ilex paraguariensis*) on the expression of the leukocyte NADPH oxidase subunit p47phox and on circulating inflammatory cytokines in healthy men: a pilot study. Int. J. Food Sci. Nutr. 70, 212-221DOI:10.1080/09637486.2018.1486393.
Phenolaeis.com Accessed Aug. 24, 2022 Palm Fruit Extract compositions and applications.
Phenolaeis.com Accessed Sep. 9, 2020 Palm Fruit Bioactives Complex.
Plumb G. W., et al. (1999) Metabolism of chlorogenic acid by human plasma, liver, intestine and gut microflora. J. Sci. Food Agric. 79, 390-392. DOI:10.1002/(SICI)1097-0010(19990301)79:3<390 ::AID-JSFA258>3.0.CO;2-0.
Prakash et al., "Catalytic Hydrogenation of the Sweet Principles of Stevia rebaudiana, Rebaudioside B, Rebaudioside C, and Rebaudioside D and Sensory Evaluation of Their Reduced Derivatives", Int. J. Mol. Sci. 2012, 13, 15126-15136; doi:10.3390/ijms131115126.
Prakash Indra et al: "Synthesis and Sensory Evaluation of ent-Kaurane Diterpene Glycosides", Molecules, [Online] vol. 17, No. 8, Jan. 1, 2012 (Jan. 1, 2012), pp. 8908-8916, XP055839039, DOI:10.3390/molecules17088908 Retrieved from the Internet: URL:https://www.ncbi.nlm.nih.gov/pmc/artic les/PMC6268950/pdf/molecules-17-08908.pdf> [retrieved on Aug. 5, 2021].
Prakash, "Characterization and sensory evaluation of a hexa B-D-glucopyranosyl diterpene from Stevia rebaudiana," Natural Products Communications, 2013, 8:1523-1526.
Prakash, et al., "Development of novel functional confectionery using low reduced sugar," Indian Journal of Drugs, 2016, 4(4), 141-148.
Renouf M., et al. (2014) Dose-response plasma appearance of coffee chlorogenic and phenolic acids in adults. Mol. Nutr. Food Res. 58, 301-309. DOI:10.1002/mnfr.201300349.
Richling E., et al. (2012) Dose-response relationship of chlorogenic acids in humans. Naunyn Schmiedebergs ArchPharmacol. 385, S75 [abstract 327]. DOI:10.1007/s00210-012-0736-0.
Rocha D. S., et al. (2018) Effect of yerba mate (*Ilex paraguariensis*) extract on the metabolism of diabetic rats. Biomed. Pharmacother. 105, 370-376 [plus supplementary figure]. DOI:10.1016/j.biopha.2018.05.132.
Rogerio De Sousa W., et al. (2019) Evaluation of reproductive toxicology of aqueous extract of yerba mate (*Ilex paraguariensis* A. St.-Hil.), a traditional South American beverage. J. Med. Food 22, 97-101. DOI:10.1089/jmf.2018.0060.
Rogers et al., "Changes to the content of sugars, sugar alcohols, myo-inositol, carboxylic acids and inorganic anions in developing grains from different varieties of Robusta (*Coffea canephora*) and Arabica (*C. arabica*) coffees," Plant Science, 1999, 149, 115-123.
Roy, G., "Bitterness: reduction and inhibition," Trends Food Sci Tech, 1992, 3, 85-91.
Sanchez Boado L., et al.(2018) Effects of llex paraguariensis polyphenols on magnesium absortion and iron bioavailability: preliminary study. J. Food Res. 7, 114-126. DOI:10.5539/jfr.v7n2p114.
Sarria B., et al. (2020a) Yerba mate may prevent diabetes according to a crossover, randomized, controlled study in humans. Proc. Nutr. Soc. 79, OCE2, E245 DOI:10.1017/S0029665120001937.
Sarria B., et al. (2020b) Yerba mate improves cardiovascular health in normocholesterolemic and hypercholesterolemic subjects. Proc. Nutr. Soc. 79, OCE2, E635. DOI:10.1017/S0029665120005844.
Schwarz et al., "Investigation of plant extracts for the protection of processed foods against lipid oxidation." Eur Food Res Technol, 2001, 212:319-328.
Shibata et al., "Glucosylation of steviol and steviol-glucosides in extracts from Stevia rebaudiana Bertoni," Plant Physiol., 1991, 95, 152-156.
Shinomiya K., et al. (2004) Effects of chlorogenic acid and its metabolites on the sleep-wakefulness cycle in rats. Eur. J. Pharmacol. 504, 185-189. DOI:10.1016/j.ejphar.2004.09.054.
Shiraishi et al., "Taste-Masking Effect of Chlorogenic Acid (CGA) on Bitter Drugs Evaluated by Taste Sensor and Surface Plasmon Resonance on the Basis of CGA-Drug Interactions," 2017, 65(2): 127-133, Chem Pharm Bull (Tokyo).
Simao Do Carmo L., et al. (2013) The effects of yerba maté (*Ilex paraguariensis*) consumption on IL-1, IL-6, TNF-a and IL-10 production by bone marrow cells in Wistar rats fed a high-fat diet. Int J Vitam Nutr Res 83, 26-35. DOI:10.1024/0300-9831/a000142.
Sirima Puangpraphant et al: "Dicaffeoylquinic acids in Verba mate (*Ilex paraguariensis* St. Hilaire) inhibit NF-&kgr;B nucleus translocation in macrophages and induce apoptosis by activating caspases-8 and -3 in human colon cancer cells", Molecular Nutrition & Food Research, vol. 55, No. 10, Oct. 8, 2011 (Oct. 8, 2011), pp. 1509-1522, XP055175515, ISSN: 1613-4125, DOI: 10.1002/mnfr.201100128.
Song Z., et al. (2014) [Effect of chlorogenic acid at high dose on expression of hepatic inflammatory cytokines mRNA induced by lipopolysaccharides]. Ying Yang Xue Bao [Acta Nutr. Sin.] 36, 481-485.
Song, "Lenalidomide-Gallic Acid Cocrystals with Constant High Solubility", Crystal Growth & Design, 2015, 15, pp. 4869-4875.
Souza S. J., et al. (2017) Effect of chocolate and mate tea on the lipid profile of individuals with HIV/AIDS on antiretroviral therapy: A clinical trial. Nutrition 43-44, 61-68. DOI:10.1016/j.nut.2017.06.017.

(56) References Cited

OTHER PUBLICATIONS

Stalmach A., et al. (2009) Metabolite profiling of hydroxycinnamate derivatives in plasma and urine after the ingestion of coffee by humans: identification of biomarkers of coffee consumption. Drug Metab. Dispos. 37, 1749-1758. DOI:10.1124/dmd.109.028019.
Stalmach A., et al. (2010) Bioavailability of chlorogenic acids following acute ingestion of coffee by humans with an ileostomy. Arch. Biochem. Biophys. 501, 98-105. DOI:10.1016/j.abb.2010.03.005.
Standard Method Performance Requirements (SMPRs) for Determination of Phenolic Compounds in Dietary Supplements and Dietary Ingredients Containing Echinacea, Sep. 22, 2017, AOAC International.
Stich H. F., et al. (1981) A comparative genotoxicity study of chlorogenic acid (3-O-caffeoylquinic acid). Mutat. Res. 90, 201-212. DOI:10.1016/0165-1218(81)90001-X.
Stukelj, et al., "Direct measurement of amorphous solubility," Analytical Chemistry, 2019.
Suarez-Quiroz et al., "Isolation of green coffee chlorogenic acids using activated carbon," Journal of Food Composition and Analysis, 2014, 33:55-58.
SUNUP® Commercially available stevia sweetened green coffee bean beverage, purchased Jun. 2018.
Suzuki A., et al. (2006) Chlorogenic acid attenuates hypertension and improves endothelial function in spontaneously hypertensive rats. J. Hypertens. 24, 1065-1073. DOI:10.1097/01.hjh.0000226196.67052.c0.
Sweet Drops ™ Liquid Stevia Product, 2012.
Tanaka, O., "Improvement of taste of natural sweeteners," Pure & Appl. Chem., 69(4):975-683, 1997.
Trugo et al., Chlorogenic Acid Composition of Instant Coffees, Analyst, Mar. 1984, vol. 109, pp. 263-266.
Tyrer, D., "The theory of solubility," The Journal of Physical Chemistry, 1912.
U.S. FDA (1993) Appendix I. Table 14. Conversion table for test chemical treatment doses used in PAFA. In Priority Based Assessment of Food Additives (PAFA) Database. U.S. Food and Drug Administration (U.S. FDA), Center for Food Safety & Applied Nutrition (CFSAN), Washington, DC, p. 58.
U.S. FDA (2018) Part 182-Substances generally recognized as safe. Section §182.20—Essential oils, oleoresins (solvent-free), and natural extractives (including distillates). In: U.S. Code of Federal Regulations (CFR). Title 21: Food and Drugs. (U.S. Food and Drug Administration). U.S. Government Printing Office (GPO), Washington, DC.
Ueki, T, Honda, H & Sakurai, S (1986) Analysis of Chlorogenic Acids and Caffeine in Coffee-containing Beverages by High Performance Liquid Chromatography: Reports of Surveys and Research. Saitama: Food and Agricultural Materials Inspection Center.
Upreti, Mani et al., "Solubility Enhancement of Steviol Glycosides and Characterization of Their Inclusion Complexes with Gamma-Cyclodextrin", Int. J. Mol. Sci. 2011, 12, 7529-7553.
Vargas Alves R. J., et al. (2008) The evaluation of maté (*Ilex paraguariensis*) genetic toxicity in human lymphocytes by the cytokinesis-block in the micronucleus assay. Toxicol. In Vitro 22, 695-698. DOI:10.1016/j.tiv.2007.11.005.
Wang Y., et al. (2018) [Effects of chlorogenic acid on growth performance, serum immunoglobulins, intestinal mucosa morphology, digestive and absorptive capacity of piglets]. Chin. J. Anim. Nutr. 30, 1136-1145 [DOI:10.7506/spkx1002-6630-201709026.
Wantanabe T., et al. (2019) Coffee abundant in chlorogenic acids reduces abdominal fat in overweight adults: a randomized, double-blind, controlled trial. Nutrients 11, 1617 [13pp]. DOI:10.3390/nu11071617.
Wei Z.-M., et al. (2010) [Clinical tolerability of 1,5-dicaffeoylquinic acid tablets]. Zhongguo Xin Yao Za Zhi [Chin. J. New Drugs] 19, 106-108.
Weidel et al., "A Rapid Method for Quantifying Chlorogenic Acid Levels in Potato Samples," Journal of AOAC International, vol. 97, No. 3, Nov. 3, 2014.

Whole Foods 365 Stevia Extract Liquid, 2012.
Wildermuth et al., "Chlorogenic acid oxidation and its reaction with sunflower proteins to form green-colored complexes," Comprehensive Reviews in Food Science and Food Safety, 2016, vol. 15, 829-843.
Wnuk M., et al. (2009) Evaluation of the cyto- and genotoxic activity of yerba mate (*Ilex paraguariensis*) in human lymphocytes in vitro. Mutat. Res. 679, 18-23. DOI:10.1016/j.mrgentox.2009.07.017.
Written Opinion of WO 2012/082587, Jun. 13, 2013.
Yang B., et al. (2005) Metabolic profile of 1,5-dicaffeoylquinic acid in rats, an in vivo and in vitro study. Drug Metab. Dispos. 33, 930-936. DOI:10.1124/dmd.104.002154.
Yara Queiroz et al: The Chlorogenic Acid and Caffeine Content of Verba Mate (*Ilex paraguariensis*) Beverages11, Jan. 1, 2005 (Jan. 1, 2005), pp. 91-95, XP055715126, Retrieved from the Internet: URL:https://media.enfasis.com/adjuntos/146 /documentos/000/134/0000134821.pdf [retrieved on Jul. 15, 2020].
Yu S., et al. (2015) Yerba mate (*Ilex paraguariensis*) improves microcirculation of volunteers with high blood viscosity: a randomized, double-blind, placebo-controlled trial. Exp. Gerontol. 62, 14-22 [plus supplementary tables]. DOI:10.1016/j.exger.2014.12.016.
Zhu Y., et al. (2017) [Effect of caffeine and chlorogenic acid on body weight, lipid accumulation and the expression of lipid metabolism-related genes in high-fat diet-fed mice]. Shipin Kexue [Food Sci.] 38, 162-167 DOI:10.7506/spkx1002-6630-201709026.
Zuniga L. Y., et al. (2018) Effect of chlorogenic acid administration on glycemic control, insulin secretion, and insulin sensitivity in patients with impaired glucose tolerance. J. Med. Food 21, 469-473. DOI:10.1089/jmf.2017.0110.
Freedman S. O., et al. (1961) Chlorogenic acid: an allergen in green coffee bean. Nature 192, 241-243. DOI:10.1038/192241a0.
Freedman S. O., et al. (1964) Antigenic and allergenic properties of chlorogenic acid man, rabbit, guinea pig. Can. Med. Assoc. J. 90, 473-474.
Fu et al., "Production of chlorogenic acid and its derivatives in hairy root cultures of Stevia rebaudiana," Jan. 14, 2015, Journal of Agriculatural and Food Chemistry, 63(1):262-268.
Gawel-Beben et al., "Stevia rebuadiana Bert. Leaf extracts as a multifunctional source of natural antioxidants," Molecules, Mar. 27, 2015.
Gebara K. S., et al. (2020) A randomized crossover intervention study on the effect a standardized maté extract (*Ilex paraguariensis* A. St.-Hil.) in Men predisposed to cardiovascular risk. Nutrients, 13, 14 [14pp]. DOI:10.3390/nu13010014.
Giordani, Antonio, "The amorphous form in drug development," Crystal Forms, 2012.
Gómez-Juaristi M., Martínez-López S., Sarria B., Bravo L. and Mateos R. (2018) Absorption and metabolism of yerba mate phenolic compounds in humans. Food Chem. 240, 1028-1038. DOI:10.1016/j.foodchem.2017.08.003.
Gonthier M.-P., et al. (2006) Microbial metabolism of caffeic acid and its esters chlorogenic and caftaric acids by human faecal microbiota in vitro. Biomed. Pharmacother. 60, 536-540. DOI:10.1016/j.biopha.2006.07.084.
Grzesiuk J. D., et al.(2012) Evaluation of mutagenicity and antimutagenicity of Ilex paraguariensi} A. St.-Hil.: Aquifoliaceae infusion on Allium cepa assay. Arq. Cienc. Saude UNIPAR 16, 73-78. DOI:10.25110/arqsaude.v1612.2012.4840.
Gu R., et al. (2007) Simultaneous determination of 1,5-dicaffeoylquinic acid and its active metabolites in human plasma by liquid chromatography-tandem mass spectrometry for pharmacokinetic studies. J. Chromatogr. B. 852, 85-91. DOI:10.1016/j.jchromb.2006.12.055.
Hancock, B. C., et al. "What is the true solubility advantage for amorphous pharmaceuticals?," Pharm Res, 17:397-404, 2000.
Hernandes L. C., et al. (2016) Cytotoxicity and genotoxicity of chlorogenic acid alone or associated with the demethylating drug 5-azacytidine in Jurkat cells. Toxicol. Lett. 258, Suppl. S, S56 [abstract OSC01-007]. DOI:10.1016/j.toxlet.2016.06.1295.

(56) References Cited

OTHER PUBLICATIONS

Hernandez T et al., "Variations in the phenolic composition of fruit juices with different treatments," European Food Research and Technology, vol. 204, No. 2, 1997, p. 151-155.
Hildebrand, Joel, "Theory of solubility," Physical Review, 1923.
IARC (1991) Mate. In Coffee, Tea, Mate, Methylxanthines and Methylglyoxal. IARC Working Group, Feb. 27-Mar. 6, 1990, Lyon. IARC Monographs on the Evaluation of Carcinogenic Risks to Humans, vol. 51, pp. 273-287. World Health Organization (WHO), International Agency for Research on Cancer (IARC).
IARC (2018) Drinking mate and very hot beverages. In Drinking Coffee, Mate, and Very Hot Beverages. Expert Opinions of IARC Working Group on the Evaluation of Carcinogenic Risks to Humans, May 24-31, 2016, Lyon, France. IARC Monographs on the Evaluation of Carcinogenic Risks to Humans, vol. 116, pp. 427-496. Lyon, France: International Agency for Research on Cancer (IARC), Lyon, France.
International Search Report and Written Opinion mailed Jul. 28, 2020 of PCT/US2020/026524 (14 pages).
Islam, et al., "Particle crystallization during spray drying in humid air," Journal of Food Engineering, 2010.
Jeon et al., "Contents of chlorogenic acids and caffeine in various coffee-related products," Journal of Advanced Research, 17 (2019), 85-94.
Jin S., et al. (2015) Chlorogenic acid improves late diabetes through adiponectin receptor signaling pathways in db/db mice. PLoS One 10, e0120842 [15pp]. DOI:10.1371/journal.pone.0120842.
Journal of the Brewing Society of Japan, 1959, vol. 54, No. 4, pp. 239-242.
Julia Y.Q. Low et al., "Psychophysical Evaluation of Sweetness Functions Across Multiple Sweeteners", Chemical Senses., vol. 42, No. 2, Oct. 20, 2016 (Oct. 20, 2016), p. 111-120.
Kato M., et al. (2018) Effect of chlorogenic acid intake on cognitive function in the elderly: a pilot study. Evid. Based. Complement. Alternat. Med. 2018, Article ID 8608497 [8pp]. DOI:10.1155/2018/8608497.
Kellie P Burris et al, "Composition and Bioactive Properties of Yerba Mate (*Ilex paraguariensis* A. St .- Hil.): A Review", Chillán Jun. 2012 (Jun. 2012), p. 268-275.
Kim H. J., et al. (2012) Effect of green mate in overweight volunteers: a randomised placebo-controlled human study. J. Funct. Foods 4, 287-293. DOI:10.1016/j.jff.2011.12.005.
Kim S.-Y., et al. (2015) Anti-obesity effects of Yerba Mate (*Ilex paraguariensis*): a randomized, double-blind, placebo-controlled clinical trial. BMC Complement. Altern. Med. 15, 338 [8pp]. DOI:10.1186/s12906-015-0859-1.
Klein G. A., et al.(2011) Mate tea (*Ilex paraguariensis*) improves glycemic and lipid profiles of type 2 diabetes and pre-diabetes individuals: a pilot study. J. Am. Coll. Nutr. 30, 320-332.
Kremr et al., "Unremitting Problems with Chlorogenic Acid Nomenclature: A Review," Quim. Nova, vol. 39, No. 4, 530-533, 2016.
Kren, V., et al., "Glycosides in Medicine: The Role of Glycosidic Residue in Biological Activity", Current Medicinal Chemistry, 2001, 8, 1313-1338.
Kroyer, G., "Stevioside and Stevia-sweetener in food: application, stability and interaction with food ingredients," J. Verbr. Lebensm., 2010, 5:225-229.
Kujawska M (2018) Yerba mate (*Ilex paraguariensis*) beverage: nutraceutical ingredient or conveyor for the intake of medicinal plants? Evidence from Paraguayan folk medicine. Evid. Based. Complement. Alternat. Med. 2018, Article ID 6849317 [17pp]. DOI:10.1155/2018/6849317.
Ky et al., "Camparison of Five Purification Methods for Chlorogenic Acids in Green Coffee Beans (*Coffea* sp.)," J. Agric. Food Chem. 1997, 45, 786-790, obtained from https://horizon.documentation.ird.fr/exl-doc/pleins_textes/pleins_textes_6/b_fdi_47-48/010010457.pdf.
Laird Layton L., et al. (1964) Pure chlorogenic acid is not allergenic in atopy to green coffee: A specific protein probably is involved. Nature 203, 188-189. DOI:10.1038/203188a0.

Lee et al., "Chicoric acid: chemistry distribution, and production," Frontiers in Chemistry, 2013, 1(40).
Leitão A. C. and Braga R. S. (1994) Mutagenic and genotoxic effects of mate (*Ilex paraguariensis*) in prokaryotic organisms. Braz. J. Med. Biol. Res. 27, 1517-1525.
Lin M., et al. (2013) Evaluation of the potential sensitization of chlorogenic Acid: a meta-analysis. Evid. Based. Complement. Alternat. Med. 2013, Article ID 208467 DOI:10.1155/2013/208467.
Liquid Stevia and Liquid Stevia (flavored) from Stevita Co., 2012.
Liu B., et al. (2017) Preparation, phytochemical investigation, and safety evaluation of chlorogenic acid products from Eupatorium adenophorum. Molecules 22, 67 [12pp]. DOI:10.3390/molecules22010067.
Liu Z., et al. (2010) Evaluation of the immunosensitizing potential of chlorogenic acid using a popliteal lymph node assay in BALB/c mice. Food Chem. Toxicol. 48, 1059-1065. DOI:10.1016/j.fct.2010.01.024.
Lorena Deladino et al: "Major Phenolics in Yerba Mate Extracts (*Ilex paraguariensis*) and Their Contribution to the Total Antioxidant Capacity", Food and Nutrition Sciences, vol. 04, Aug. 1, 2013 (Aug. 1, 2013), pp. 154-162, XP055588480,ISSN: 2157-944X, DOI: 10.4236/fns.2013.48A019.
Lowell F. C. (1965) Allergenicity of chlorogenic acid. J. Allergy 36, 308. DOI:10.1016/0021-8707(65)90091-2.
Maietta et al., "Artichoke (*Cynara cardunculus* L. var. scolymus) waste as a natural source of carbonyl trapping and antiglycative agents," Food Research International, 100 (2017) 780-790.
Marques V. X. and Farah A. (2010) Urinary excretion of chlorogenic acids and metabolites in humans after green mate (*I. paraguariensis*) consumption. FASEB J. 24, 1, Suppl., [abstract 922.1]. DOI:10.1096/fasebj.24.1_supplement.922.1.
Masuda, et al., "Powder Technology Handbook," Taylor & Francis, 2006.
Matsumoto R. L. T., et al. (2009) Effects of maté tea (*Ilex paraguariensis*) ingestion on mRNA expression of antioxidant enzymes, lipid peroxidation, and total antioxidant status in healthy young women. J. Agric. Food Chem. 57, 1775-1780. DOI:10.1021/jf803096g.
Meilgaard MC, Civille GV, and Carr BT (2007). Sensory Evaluations Techniques, CRC Press, Boca Raton, FL.
Meinhart et al., "Analysis of chlorogenic acids isomers and caffeic acid in 89 herbal infusions (tea)," Journal of Food Composition and Analysis, 73 (2018) 76-82.
Meinhart et al., "Chlorogenic acid isomer contents in 100 plants commercialized in Brazil," Food Research International, 99 (2017) 522-530.
Meireles et al., "Stevia (*Stevia rebaudiana* Bertoni):—Futuristic view of the sweeter side of life," Floriculture, Ornamental and Plant Biotechnology vol. IV, 2006, Global Science Books.
Mello F. W., et al. (2018) Maté consumption association with upper aerodigestive tract cancers: a systematic review and meta-analysis. Oral Oncol. 82, 37-47 [plus supplementary data]. DOI:10.1016/j.oraloncology.2018.04.023.
Alibaba ] [Online], "Yerba mate herbal tea", Online available at < < URL:https://japanese.alibaba.com/g/yerba-mate-herbal-tea.html, Dec. 25, 2024, 5 pages.
Alma Japan] [Online], "Yerba Mate Organic Lemon Ginger Tea", Online available at << URL:https://www.almajapan.com/product.asp?CD=MJ0006>, Dec. 25, 2024, 2 pages.
Amazon [Online], May 16, 2018 [search date Dec. 25, 2024], Internet "BALIBETOV Stainless Steel Double Wall Mate Cup and Bombilla Set—Yerba Mate Set includes 1 Yerba Mate Cup, 2 Bombillas Mate and Brush—Easy Care (Black)", Online Available at << URL:https://amzn.asia/d/3fGkSL6>.
Filip et al., "Phenolic compounds in seven South American *Ilex* species", Fitoterapia, vol. 72, No. 7, 2001, pp. 774-778.
Hartwig et al., "A Total Polyphenol Content of Mate (*Ilex paraguariensis*) and Other Plants-derived Beverages", Journal of Food Research, vol. 1, No. 3, May 29, 2012, pp. 58-67.
Heck et al., "Yerba Mate Tea (*Ilex paraguariensis*): a comprehensive review on chemistry, health implications, and technological considerations", Journal of food science, vol. 72, No. 9, 2007, pp. R138-R151.

(56) References Cited

OTHER PUBLICATIONS

Karaköse et al., "Characterization and Quantification of Hydroxycinnamate Derivatives in Stevia rebaudiana Leaves by LCMSn", Journal of Agricultural and Food Chemistry, vol. 59, No. 18, 2011, pp. 10143-10150.

Karaköse et al., "Profiling and Quantification of Phenolics in Stevia rebaudiana Leaves", Journal of Agricultural and Food Chemistry, vol. 63, No. 41, Oct. 21, 2015, pp. 9188-9198.

Kaushik et al., "Nutrient composition of cultivated stevia leaves and the influence of polyphenols and plant pigments on sensory and antioxidant properties of leaf extracts", Journal of Food Science and Technology, vol. 47, No. 1, Jan. 2010, pp. 27-33.

Sytar et al., "Antioxidant Activity and Phenolics Composition in Stevia Rebaudiana Plants of Different Origin", Journal of Microbiology Biotechnology and Food Sciences, vol. 5, No. 3, 2015, pp. 221-224.

Wolwer-Rieck, "The Leaves of Stevia rebaudiana (Bertoni), Their Constituents and the Analyses Thereof: A Review", Journal of Agricultural and Food Chemistry, vol. 60, No. 4, 2012, pp. 886-895.

\* cited by examiner

US 12,419,335 B2

READILY DISSOLVABLE STEVIOL GLYCOSIDE COMPOSITIONS

CROSS-REFERENCE TO RELATED APPLICATIONS

This application is a Continuation of U.S. application Ser. No. 16/753,869, filed Apr. 6, 2020, which is a national phase application of PCT Application No. PCT/US2018/054698, filed Oct. 5, 2018, which claims the benefit of U.S. Provisional Application No. 62/569,279, filed Oct. 6, 2017, and U.S. Provisional Application No. 62/676,722, filed May 25, 2018, each of which is incorporated by reference in its entirety.

BACKGROUND

Steviol glycosides are glycosides of steviol, a diterpene compound and are about 150 to 450 times sweeter than sugar. Examples of steviol glycosides are described in WO 2013/096420 (see, e.g., listing in FIG. 1); and in Ohta et. al., "Characterization of Novel Steviol Glycosides from Leaves of Stevia rebaudiana Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2a-2k. See also PCT Patent Publication WO 20013/096420. Steviol glycosides can include one or more of dulcoside A, stevioside, and one or more of rebaudioside A, B, C, D, E, F, G, H, I, J, K, L, M, N, O, steviolbioside and rubusoside. Steviol glycosides have found use as non-caloric high intensity sweetener in foods and beverages.

SUMMARY

The present disclosure generally relates to readily dissolvable steviol glycoside solutions comprising a steviol glycoside and a steviol glycoside dissolution enhancer compound (SG dissolution enhancer). One aspect provides a readily dissolvable steviol glycoside composition comprising a steviol glycoside and a dissolution enhancer compound in an amount effective to increase dissolution of the steviol glycoside, wherein the dissolution enhancer compound comprises at least one compound selected from the group consisting of a quinic acid, caffeic acid, ferulic acid, sinapic acid, p-coumaric acid, an ester of quinic acid, an ester of caffeic acid, an ester of ferulic acid, an ester of sinapic acid, an ester of p-coumaric acid, an ester of caffeic acid and quinic acid, an ester of caffeic acid and quinic acid comprising a single caffeic acid moiety, an ester of caffeic acid and quinic acid comprising more than one caffeic acid moiety, an ester of ferulic acid and quinic acid, an ester of ferulic acid and quinic acid comprising a single ferulic acid moiety, an ester of ferulic acid and quinic acid comprising more than one ferulic acid moiety, an ester of sinapic acid and quinic acid, an ester of sinapic acid and quinic acid comprising a single sinapic acid moiety, an ester of sinapic acid and quinic acid comprising more than one sinapic acid moiety, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety, a caffeic ester of 3-(3,4-dihydroxyphenyl)lactic acid, an ester of caffeic acid and tartaric acid, an ester of caffeic acid and tartaric acid comprising a single caffeic acid moiety, an ester of caffeic acid and tartaric acid comprising more than one caffeic acid moiety, salts thereof, and/or isomers thereof. In some aspects, the amount effective to increase dissolution of the steviol glycoside is an amount such that the dissolution enhancer compound comprises a 1:0.3 to 1:3 ratio by weight of steviol glycoside to dissolution enhancer compound. In other aspects, the amount effective to increase dissolution of the steviol glycoside is an amount such that the dissolution enhancer compound comprises a 1:1 to 1:3 ratio by weight of steviol glycoside to dissolution enhancer compound.

In some aspects, the dissolution enhancer compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, rosmarinic acid, cichoric acid, caftaric acid, monocaffeoyltartaric acids, dicaffeoyltartaric acids and salts and/or isomers thereof. In other aspects, the dissolution enhancer compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid. In some aspects, the dissolution enhancer compound comprises one or more compounds selected from the group consisting of 3-O-coumaroylquinic acid, 4-O-coumaroylquinic acid, 5-O-coumaroylquinic acid, 3,4-dicoumaroylquinic acid, 3,5-dicoumaroylquinic acid, and 4,5-dicoumaroylquinic acid.

In some aspects, the steviol glycoside is crystalline. In other aspects, the steviol glycoside comprises rebaudioside M. In some aspects, the steviol glycoside comprises rebaudioside D. In other aspects, the steviol glycoside comprises rebaudioside A.

In some aspects, the composition is a dry mixture. In other aspects, the composition is an admixture of steviol glycoside and dissolution enhancer compound. In some aspects, the composition is prepared by co-drying steviol glycoside and dissolution enhancer compound.

In some aspects, the dissolution enhancer compound is prepared from a botanical source. In other aspects, the botanical source is selected from the group consisting of eucommoia ulmoides, honeysuckle, *Nicotiana benthamiana*, globe artichoke, cardoon, *stevia, Stevia rebaudiana*, monkfruit, coffee, coffee beans, green coffee beans, tea, white tea, yellow tea, green tea, oolong tea, black tea, red tea, post-fermented tea, bamboo, heather, sunflower, blueberries, cranberries, bilberries, grouseberries, whortleberry, lingonberry, cowberry, huckleberry, grapes, chicory, eastern purple coneflower, *echinacea*, Eastern pellitory-of-the-wall, Upright pellitory, Lichwort, Greater celandine, Tetterwort, Nipplewort, Swallowwort, Bloodroot, Common nettle, Stinging nettle, Potato, Potato leaves, Eggplant, Aubergine, Tomato, Cherry tomato, Bitter apple, Thorn apple, Sweet potato, apple, Peach, Nectarine, Cherry, Sour cherry, Wild cherry, Apricot, Almond, Plum, Prune, Holly, Yerba mate, Mate, *ilex paraguariensis*, Guayusa, Yaupon Holly, Kuding, Guarana, Cocoa, Cocoa bean, Cacao, Cacao bean, Kola nut, Kola tree, Cola nut, Cola tree, Hornwort, Ostrich fern, Oriental ostrich fern, Fiddlehead fern, Shuttlecock fern, Oriental ostrich fern, Asian royal fern, Royal fern, Bracken, Brake, Common bracken, Eagle fern, Eastern brakenfern, dandelion, algae, seagrasses, Clove, Cinnamon, Indian bay leaf, Nutmeg, Bay laurel, Bay leaf, Basil, Great basil, Saint-Joseph's-wort, Thyme, Sage, Garden sage, Common sage, Culinary sage, Rosemary, Oregano, Wild marjoram, Marjoram, Sweet marjoram, Knotted marjoram, Pot marjoram, Dill, Anise, Star anise, Fennel, Florence fennel, Tarragon, Estragon, Mugwort, Licorice, Liquorice, Soy, Soybean, Soya bean, Wheat, Common wheat, Rice, Canola, Broccoli, Cauliflower, Cabbage, Bok choy, Kale, Collard greens, Brussels sprouts, Kohlrabi, Winter's bark, Elderflower, Assa-Peixe, Greater burdock, Valerian, and Chamomile. In some aspects, the botanical source is yerba mate. In other aspects, the botanical source is rosemary. In some aspects, the botanical source is chicory. In other aspects, the botanical source is *stevia*. In other aspects, the botanical source is globe artichoke. In some aspects, the botanical source is green coffee bean.

One aspect provides a readily dissolvable dry steviol glycoside composition comprising a steviol glycoside and a dissolution enhancer compound in an amount effective to increase dissolution of the steviol glycoside, wherein the dissolution enhancer compound comprises at least one caffeic ester of quinic acid, caffeic ester of 3-(3,4-dihydroxyphenyl)lactic acid, caffeic acid ester of tartaric acid, ferulic ester of quinic acid, and/or isomers thereof, and wherein the composition is a dry mixture. In some aspects, the dissolution enhancer compound comprises at least 15% dicaffeoylquinic acid. In other aspects, the amount effective to increase dissolution of the steviol glycoside is an amount such that the dissolution enhancer compound comprises a 1:0.3 to 1:3 ratio by weight of steviol glycoside to dissolution enhancer compound. In some aspects, the amount effective to increase dissolution of the steviol glycoside is an amount such that the dissolution enhancer comprises a 1:1 to 1:3 ratio by weight of steviol glycoside to dissolution enhancer. In other aspects, the composition comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

In some aspects, the caffeic ester of quinic acid comprises at least one of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, or 4,5-dicaffeoylquinic acid. In other aspects, the ferulic ester of quinic acid comprises at least one of 3-O-feruloylquinic acid, 4-O-feruloylquinic acid, 5-O-feruloylquinic acid, 3,4-diferuloylquinic acid, 3,5-diferuloylquinic acid, or 4,5-diferuloylquinic acid. In some aspects, the caffeic ester of 3-(3,4-dihydroxyphenyl)lactic acid comprises rosmarinic acid. In other aspects, the caffeic acid ester of tartaric acid comprises cichoric acid. In other aspects, the caffeic acid ester of tartaric acid comprises caftaric acid.

In some aspects, the steviol glycoside is crystalline. In other aspects, the steviol glycoside comprises rebaudioside M. In some aspects, the steviol glycoside comprises rebaudioside D. In other aspects, the steviol glycoside comprises rebaudioside A. In some aspects, the dry composition is an admixture of steviol glycoside and dissolution enhancer compound. In other aspects, the dry composition is prepared by co-drying steviol glycoside and dissolution enhancer compound.

In some aspects, the dissolution enhancer compound is prepared from a botanical source. In other aspects, the botanical source is selected from the group consisting of eucommoia ulmoides, honeysuckle, *Nicotiana benthamiana*, globe artichoke, cardoon, *stevia, Stevia rebaudiana*, monkfruit, coffee, coffee beans, green coffee beans, tea, white tea, yellow tea, green tea, oolong tea, black tea, red tea, post-fermented tea, bamboo, heather, sunflower, blueberries, cranberries, bilberries, grouseberries, whortleberry, lingonberry, cowberry, huckleberry, grapes, chicory, eastern purple coneflower, *echinacea*, Eastern pellitory-of-the-wall, Upright pellitory, Lichwort, Greater celandine, Tetterwort, Nipplewort, Swallowwort, Bloodroot, Common nettle, Stinging nettle, Potato, Potato leaves, Eggplant, Aubergine, Tomato, Cherry tomato, Bitter apple, Thorn apple, Sweet potato, apple, Peach, Nectarine, Cherry, Sour cherry, Wild cherry, Apricot, Almond, Plum, Prune, Holly, Yerba mate, Mate, *ilex paraguariensis*, Guayusa, Yaupon Holly, Kuding, Guarana, Cocoa, Cocoa bean, Cacao, Cacao bean, Kola nut, Kola tree, Cola nut, Cola tree, Hornwort, Ostrich fern, Oriental ostrich fern, Fiddlehead fern, Shuttlecock fern, Oriental ostrich fern, Asian royal fern, Royal fern, Bracken, Brake, Common bracken, Eagle fern, Eastern brakenfern, dandelion, algae, seagrasses, Clove, Cinnamon, Indian bay leaf, Nutmeg, Bay laurel, Bay leaf, Basil, Great basil, Saint-Joseph's-wort, Thyme, Sage, Garden sage, Common sage, Culinary sage, Rosemary, Oregano, Wild marjoram, Marjoram, Sweet marjoram, Knotted marjoram, Pot marjoram, Dill, Anise, Star anise, Fennel, Florence fennel, Tarragon, Estragon, Mugwort, Licorice, Liquorice, Soy, Soybean, Soya bean, Wheat, Common wheat, Rice, Canola, Broccoli, Cauliflower, Cabbage, Bok choy, Kale, Collard greens, Brussels sprouts, Kohlrabi, Winter's bark, Elderflower, Assa-Peixe, Greater burdock, Valerian, and Chamomile. In some aspects, the botanical source is yerba mate, rosemary, chicory, globe artichoke, green coffee bean, and/or *stevia*.

DETAILED DESCRIPTION

This disclosure relates generally to readily dissolvable steviol glycoside compositions comprising a steviol glycoside and a steviol glycoside dissolution enhancer compound (SG dissolution enhancer) in an amount effective to increase dissolution of the steviol glycoside.

An example of a readily dissolvable steviol glycoside composition is a composition comprising a steviol glycoside and a dissolution enhancer compound in an amount effective to increase dissolution of the steviol glycoside.

In some aspects, the term dissolution refers to the process of dissolving a solute (e.g., a steviol glycoside composition) into a solvent (e.g., a primarily aqueous solution) to make a solution (e.g., a steviol glycoside solution). Dissolution can also be thought of in terms of rate at which a solute dissolves into a solvent to make a solution. For example, the rate of dissolution or dissolution rate refers to a rate at which a solute dissolves into a solvent to make a solution (e.g., the rate at which a steviol glycoside composition dissolves into a primarily aqueous solution to make a steviol glycoside solution). The rate of solution can also be used to refer to a rate at which a solute interacts with a solvent to form a solution. In some aspects, rate of dissolution and rate of solution can be used interchangeably. In other aspects, the term instantaneous solubility can refer to having a high rate of dissolution and/or a high rate of solution. For example, instantaneous solubility can refer to having a high initial dissolution of a steviol glycoside compound into a primarily aqueous solution upon mixing.

In some aspects, the term readily dissolvable composition refers to a composition with a high rate of dissolution into certain solvents. A readily dissolvable composition can exhibit a high rate of dissolution or a high rate of solution into certain solvents. A readily dissolvable composition can also comprise instantaneous solubility into certain solvents. For example, a readily dissolvable steviol glycoside composition can comprise a high rate of dissolution into a primarily aqueous solution to yield a steviol glycoside solution. A readily dissolvable steviol glycoside composition can also have a high instantaneous solubility into a primarily aqueous solution to yield a steviol glycoside solution.

The steviol glycoside composition can include one or more steviol glycosides. Exemplary steviol glycosides include rebaudioside M, rebaudioside D, rebaudioside A, rebaudioside B, reaudioside O, and rebaudioside N. In some aspects, the one or more of the steviol glycosides are produced by fermentation by an engineered organism. For example, rebaudioside D and M can be produced by an engineered organism and then isolated to produce a steviol glycoside composition of primarily rebaudioside D and rebaudioside M as the predominant steviol glycoside species. In other aspects, the steviol glycoside composition can comprise rebaudioside D and rebaudioside M in an amount greater than other steviol glycosides. In some aspects, one or more of the steviol glycosides are isolated from *Stevia rebaudiana*.

The steviol glycoside composition can include one or more steviol glycosides. In some aspects, the term steviol glycoside refers to Rebaudioside A (Reb A) (CAS #58543-16-1), Rebaudioside B (Reb B) (CAS #58543-17-2), Rebaudioside C (Reb C) (CAS #63550-99-2), Rebaudioside D (Reb D) (CAS #63279-13-0), Rebaudioside E (Reb E) (CAS #63279-14-1), Rebaudioside F (Reb F) (CAS #438045-89-7), Rebaudioside M (Reb M) (CAS #1220616-44-3), Rubusoside (CAS #63849-39-4), Dulcoside A (CAS #64432-06-0), Rebaudioside I (Reb I) (MassBank Record: FU000332), Rebaudioside Q (Reb Q), Rebaudioside O (Reb O), Rebaudioside N (Reb N) (CAS #1220616-46-5), 1,2-Stevioside (CAS #57817-89-7), 1,3-Stevioside (Reb G), Steviol-1,2-Bioside (MassBank Record: FU000299), Steviol-1,3-Bioside, Steviol-13-O-glucoside (13-SMG), Steviol-19-O-glucoside (19-SMG), and steviol glycoside having 1, 2, 3, 4, 5, 6, 7, 8, 9, 10 or sugar additions (e.g., glucose, rhamnose, and/or xylose), and isomers thereof. See FIG. 1; see also, Steviol Glycosides Chemical and Technical Assessment 69th JECFA, 2007, prepared by Harriet Wallin, Food Agric. Org.

In some aspects, the steviol glycoside composition can optionally be described in terms of amounts of rebaudioside M and rebaudioside D. For example, rebaudioside M and rebaudioside D can be present in the composition in a total amount of about 80% (wt) or greater, 90% (wt) or greater, 95% (wt), 99% (wt) or greater, of a total amount steviol glycosides in the composition. Rebaudioside M can be the predominant steviol glycoside in the composition, and can be present, for example, in an amount in the range of about 50% to about 95%, about 70% to about 90%, or about 75% to about 85% of the total amount steviol glycosides in the composition. Rebaudioside D can be in an amount less than Rebaudioside M, such as in an amount in the range of about 5% to about 25%, about 10% to about 20%, or about 10% to about 15% of the total amount steviol glycosides in the composition. In other aspects, a steviol glycoside composition comprising about 80% (wt) rebaudioside M can be referred to as RM80. The composition can also optionally be expressed in terms of amounts of other known steviol glycosides that are present in lower amounts. For example, the composition can comprise mostly rebaudioside M and/or D and can include one or more of rebaudioside A, rebaudioside B, or stevioside in an amount of about 5% (wt) or less, about 2% (wt) or less, or about 1% (wt) or less, of a total amount steviol glycosides in the composition.

In some aspects, the steviol glycoside composition can optionally be described in terms of amounts of rebaudioside A. For example, rebaudioside A can be present in the composition in a total amount of about 80% (wt) or greater, 85% (wt) or greater, 90% (wt) or greater, 95% (wt) or greater, 98% (wt) or greater of a total amount of steviol glycosides in the composition. Rebaudioside A can be the predominant steviol glycoside in the composition, and can be present, for example, in an amount in the range of about 50% to about 98%, about 70% to about 98%, or about 90% to about 98% of the total amount steviol glycosides in the composition. Other rebaudiosides can be present in an amount less than Rebaudioside A, such as in an amount in the range of about 1% to about 40%, about 1% to about 20%, or about 10% to about 15% of the total amount steviol glycosides in the composition. In other aspects, a steviol glycoside composition comprising about 95% (wt) rebaudioside A can be referred to as RA95.

In some aspects, the steviol glycoside is in a crystalline form. The term crystalline form can refer to steviol glycoside that comprises individual macroscopic crystals of steviol glycoside wherein the individual macroscopic crystals comprise steviol glycoside structured into a crystal lattice. The term crystalline form can also refer to steviol glycoside that comprises polycrystals of steviol glycoside wherein the polycrystals comprise many crystals of steviol glycoside. In some aspects, steviol glycoside in crystalline form can be produced by an organic solvent crystallization of a steviol glycoside solution. In other aspects, steviol glycoside in crystalline form can be produced by an aqueous crystallization of a steviol glycoside solution. In other aspects, purification of steviol glycoside from crude steviol glycoside extracts results in a purified steviol glycoside in a crystalline form. A crystalline form comprising crystals with an ordered lattice structure is contrasted with an amorphous form in which the solid has no periodic arrangement of the molecules.

In some aspects, steviol glycoside in a crystalline form can have a reduced rate of dissolution in a primarily aqueous solution when compared to an amorphous form. Steviol glycoside in a crystalline form can have a reduced rate of solution in a primarily aqueous solution. Steviol glycoside in a crystalline form can also possess low instantaneous solubility in a primarily aqueous solution.

Examples of steviol glycoside stabilizing compounds include: caffeic acid, an ester of caffeic acid, an ester of caffeic acid and quinic acid, an ester of caffeic acid and quinic acid comprising a single caffeic acid moiety (e.g., chlorogenic acid, cryptochlorogenic acid, and neochlorogenic acid; structures of each are provided herein), an ester of caffeic acid and quinic acid comprising more than one caffeic acid moiety (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid; structures of each are provided herein); ferulic acid, an ester of ferulic acid, an ester of ferulic acid and quinic acid, an ester of ferulic acid and quinic acid comprising a single ferulic acid moiety, an ester of ferulic acid and quinic acid comprising more than one ferulic acid moiety; quinic acid, an ester of quinic acid; tartaric acid, a tartaric acid derivative, an ester of tartaric acid (e.g. caftaric acid or cichoric acid), an ester of a tartaric acid derivative, 3-(3,4-dihydroxyphenyl)lactic acid, a 3-(3,4-dihydroxyphenyl)lactic acid derivative, an ester of 3-(3,4-dihydroxyphenyl)lactic acid (e.g. rosmarinic acid), an ester of a 3-(3,4-dihydroxyphenyl)lactic acid derivative, p-coumaric acid, an ester of p-coumaric acid, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety; sinapic acid, an ester of sinapic acid, an ester of sinapic acid and quinic acid, an ester of sinapic acid and quinic acid comprising a single sinapic acid moiety, an ester of sinapic acid and quinic acid comprising more than one sinapic acid moiety; and 3-O-feruloylquinic acid, 4-O-feruloylquinic acid, 5-O-feruloylquinic acid, 3,4-diferuloylquinic acid, 3,5-diferuloylquinic acid, and 4,5-diferuloylquinic acid.

Caffeic acid has the structure:

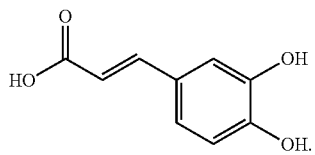 [SMILES: O=C(O)/C=C/c1ccc(O)c(O)c1]

Ferulic acid has the structure:

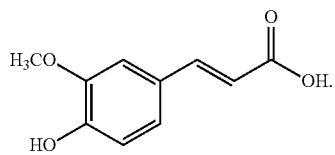 [SMILES: COc1cc(/C=C/C(=O)O)ccc1O]

p-Coumaric acid has the structure:

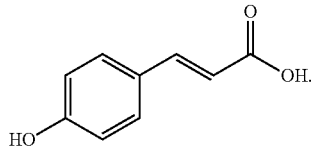 [SMILES: O=C(O)/C=C/c1ccc(O)cc1]

Sinapic acid has the structure:

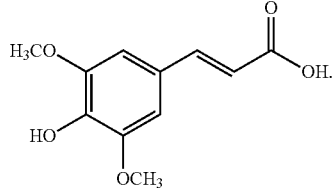

Quinic acid has the structure:

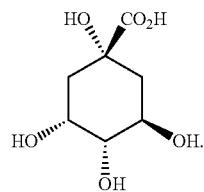 [SMILES: O=C(O)[C@]1(O)C[C@@H](O)[C@@H](O)[C@H](O)C1]

3-(3,4-dihydroxyphenyl)lactic acid has the structure:

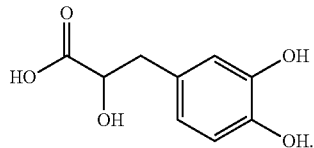 [SMILES: O=C(O)C(O)Cc1ccc(O)c(O)c1]

Tartaric acid has the structure:

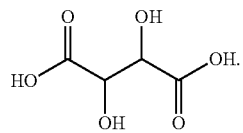

and can be in the D and L forms.

Examples of the esters of the various acids contemplated herein include the ester of caffeic acid and quinic acid, which includes monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof:

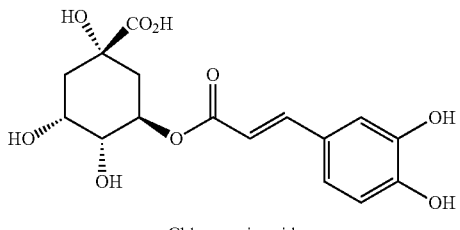

Chlorogenic acid

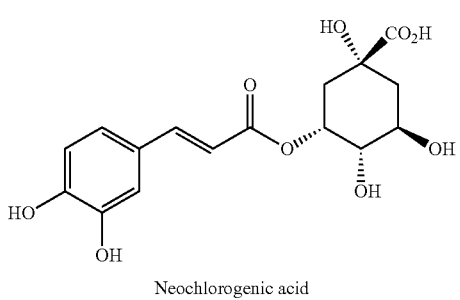

Neochlorogenic acid

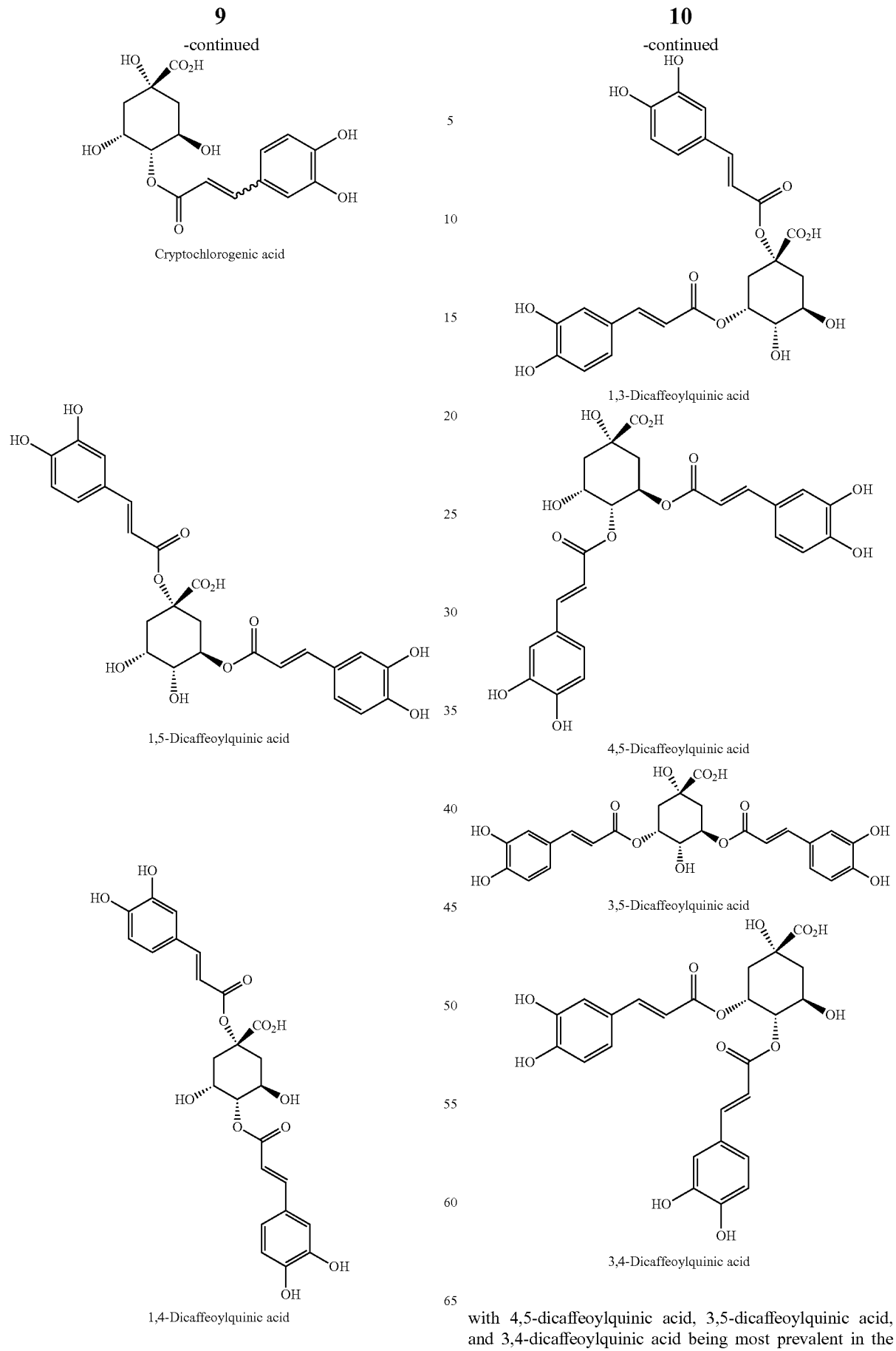
with 4,5-dicaffeoylquinic acid, 3,5-dicaffeoylquinic acid, and 3,4-dicaffeoylquinic acid being most prevalent in the compositions contemplated herein and most prevalent in abundant in *stevia*, yerba mate, globe artichoke, and green coffee bean.

Examples of the esters of the various acids contemplated herein include the ester of caffeic acid and tartaric acid, which includes cichoric acid having the structure:

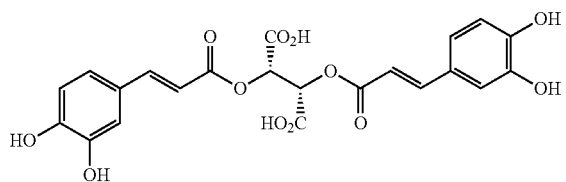 [SMILES: O=C(/C=C/c1ccc(O)c(O)c1)O[C@H](C(=O)O)[C@H](OC(=O)/C=C/c1ccc(O)c(O)c1)C(=O)O]

which has two caffeic acid molecules linked to a tartaric acid core; and caftaric acid having the structure:

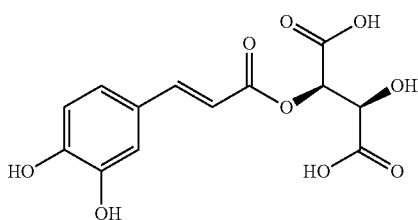 [SMILES: O=C(/C=C/c1ccc(O)c(O)c1)O[C@@H](C(=O)O)[C@@H](O)C(=O)O]

which has one caffeic acid molecule linked to a tartaric acid core.

Examples of the esters of the various acids contemplated herein include the ester of caffeic acid and 3-(3,4-dihydroxyphenyl)lactic acid including, for example, rosmarinic acid, which has the structure:

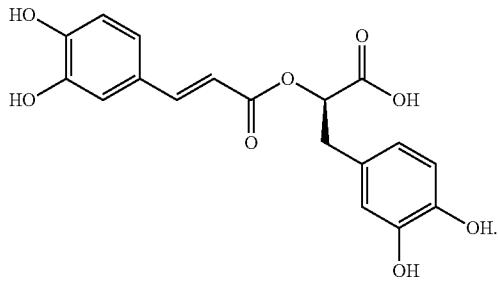 [SMILES: O=C(/C=C/c1ccc(O)c(O)c1)O[C@H](Cc1ccc(O)c(O)c1)C(=O)O]

Each of the caffeic acid, monocaffeoylquinic acids, dicaffeoylquinic acids and other dissolution enhancer compounds can be considered weak acids and can each exist in at least one of their conjugate acid form, conjugate base form (e.g., in their salt form), and mixed conjugate acid-conjugate base form, wherein a fraction (e.g., mole fraction) of the compounds exist in the conjugate acid form and another fraction exist in the conjugate base form. The fraction of conjugate acid form to conjugate base form for the caffeic acid, monocaffeoylquinic acids, dicaffeoylquinic acids, and other dissolution enhancer compounds will depend on various factors, including the pKa of each compound and the pH of the composition.

Examples of salts of caffeic acid, monocaffeoylquinic acids, dicaffeoylquinic acids, and other dissolution enhancer compounds include, but are not limited to, quaternary ammonium, sodium, potassium, lithium, magnesium, and calcium salts of caffeic acid, monocaffeoylquinic acids, dicaffeoylquinic acids, monoferuloylquinic acids, and diferuloylquinic acids, and other dissolution enhancer compounds and the like.

In some aspects, the dissolution enhancer compound can be enriched for one or more of caffeic acid, monocaffeoylquinic acids, and dicaffeoylquinic acids. The term "enriched" refers to an increase in an amount of one of caffeic acid, monocaffeoylquinic acids, and dicaffeoylquinic acids relative to one or more other compounds that are present in the dissolution enhancer compound. A dissolution enhancer compound that is enriched for one or more of caffeic acid, monocaffeoylquinic acids, and dicaffeoylquinic acids can increase dissolution of the steviol glycoside composition.

In some aspects, a dissolution enhancer compound enriched for one or more dicaffeoylquinic acids can increase dissolution of the readily dissolvable steviol glycoside composition. A dissolution enhancer compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a dissolution enhancer compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

In some aspects, the dissolution enhancer compound comprises one or more compounds selected from the group consisting of 3-O-coumaroylquinic acid, 4-O-coumaroylquinic acid, 5-O-coumaroylquinic acid, 3,4-dicoumaroylquinic acid, 3,5-dicoumaroylquinic acid, 4,5-dicoumaroylquinic acid.

In some aspects, the dissolution enhancer compound may be isolated from botanical sources. Various botanical sources comprise dissolution enhancer compound and may be used to isolate dissolution enhancer compounds. Some examples of botanical sources from which dissolution enhancer compound may be isolated include yerba mate plant (*Ilex paraguariensis*), stevia, coffee, tea, chicory, and globe artichoke. Some botanical sources may produce dissolution enhancer compound that is enriched for one or more of caffeic acid, monocaffeoylquinic acids, and dicaffeoylquinic acids and can increase dissolution of steviol glycoside composition. For example, dissolution enhancer compound isolated from yerba mate plant is enriched for dicaffeoylquinic acids and can increase dissolution of the readily dissolvable steviol glycoside composition. In other aspects, dissolution enhancer compound isolated from yerba mate plant that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

In some aspects, an amount of dissolution enhancer compound effective to increase dissolution of the steviol glycoside is an amount such that the dissolution enhancer compound comprises a 1:0.3 to 1:3 ratio by weight of steviol glycoside to dissolution enhancer compound. In other aspects, an amount of dissolution enhancer compound effective to increase dissolution of the steviol glycoside is an amount such that the dissolution enhancer compound comprises a 1:1 to 1:3 ratio by weight of steviol glycoside to dissolution enhancer compound. An amount of dissolution enhancer compound effective to increase dissolution of the steviol glycoside can be an amount such that the dissolution enhancer compound comprises a ratio by weight of steviol glycoside to dissolution enhancer compound of 1:0.1 to 1:10. In some aspects an amount of dissolution enhancer compound effective to increase dissolution of the steviol glycoside can be an amount such that the dissolution enhancer compound comprises a ratio by weight of steviol glycoside to dissolution enhancer compound of about 1:0.1 to 1:5, about 1:0.5 to 1:4, about 1:0.3 to 1:3, or about 1:1 to 1:3. In other aspects an amount of dissolution enhancer compound effective to increase dissolution of the steviol glycoside can be an amount such that the dissolution enhancer compound comprises a ratio by weight of steviol glycoside to dissolution enhancer compound of about 1:0.1, 1:0.5, 1:1, 1:2, 1:3, 1:4, 1:5, 1:6, 1:7, 1:8, 1:9, or 1:10 by weight. In some aspects, an amount of dissolution enhancer compound effective to increase dissolution of the steviol glycoside can be an amount such that the dissolution enhancer compound comprises a ratio by weight of steviol glycoside to dissolution enhancer compound of about 1:0.3 to 1:3.

In some aspects, the readily dissolvable steviol glycoside composition comprises an increased rate of dissolution in a primarily aqueous solution when compared to a steviol glycoside composition without a dissolution enhancer compound. The dissolution rate can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the dissolution rate can be increased by 1, 2, 3, 4, 5, 6, 7, 8, 9, or 10 times or more when compared to a composition without a dissolution enhancer compound.

In some aspects, the readily dissolvable steviol glycoside composition comprises an increased rate of solution in a primarily aqueous solution when compared to a steviol glycoside composition without a dissolution enhancer compound. The rate of solution can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the rate of solution can be increased by 1, 2, 3, 4, 5, 6, 7, 8, 9, or 10 times or more when compared to a composition without a dissolution enhancer compound.

In some aspects, the readily dissolvable steviol glycoside composition comprises an instantaneous solubility in a primarily aqueous solution when compared to a steviol glycoside composition without a dissolution enhancer compound. The instantaneous solubility can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a steviol glycoside composition without a dissolution enhancer compound. In other aspects, the instantaneous solubility can be increased by 1, 2, 3, 4, 5, 6, 7, 8, 9, or 10 times or more when compared to a steviol glycoside composition without a dissolution enhancer compound.

In some aspects, the readily dissolvable steviol glycoside composition comprises an increased dissolution when dissolved in a primarily aqueous solution comprises primarily water. The primarily aqueous solution can also comprise less than 1%, 5%, 10%, 15%, 20%, 30%, 40%, 45%, 50%, 55%, 60%, 65%, 70%, 80%, or 90%, or about 40% to 65%, or about 50% to 55%, or about 55% of C1-C4 alcohol (e.g., methanol, ethanol, propanol, butanol, etc.). The primarily aqueous solution can be substantially free of C1-C4 alcohols. In other aspects, the primarily aqueous solution is essentially free of C1-C4 alcohols. In some aspects, the primarily aqueous solution comprises less than 1% stevioside. The primarily aqueous solution can comprise less than 3% rebaudioside B. The primarily aqueous solution can comprise less than 1% steviolbioside. The primarily aqueous solution can comprise less than 1% 13-SMG. In other aspects, the primarily aqueous solution comprises less than one or more of 1% stevioside, 1% rebaudioside B, 1% steviolbioside, and 1% 13-SMG. In some aspects, the primarily aqueous solution has any suitable pH. The primarily aqueous solution can also comprise a pH of 0, 1, 2, 3, 4, 5, or 6. The primarily aqueous solution can comprise a pH of between 0 and 7. The primarily aqueous solution can comprise a pH of between 1 and 6. The primarily aqueous solution can comprise a pH of between 1.5 and 4.

In some aspects, the readily dissolvable steviol glycoside composition comprises an increased rate of solution in a primarily aqueous solution when compared to a steviol glycoside composition without a dissolution enhancer compound when a final concentration of steviol glycoside is between 3000 ppm and 60000 ppm. The final concentration of steviol glycoside can be greater than 100 ppm, 200 ppm, 300 ppm, 400 ppm, 500 ppm, 600 ppm, 700 ppm, 800 ppm, 900 ppm, or 1000 ppm. The final concentration of steviol glycoside can be greater than 1100 ppm, 1200 ppm, 1300 ppm, 1400 ppm, 1500 ppm, 1600 ppm, 1700 ppm, 1800 ppm, or 1900 ppm. The final concentration of steviol glycoside can be greater than 2100 ppm, 2200 ppm, 2300 ppm, 2400 ppm, 2500 ppm, 2600 ppm, 2700 ppm, 2800 ppm, or 2900 ppm. The final concentration of steviol glycoside can be greater than 3100 ppm, 3200 ppm, 3300 ppm, 3400 ppm, 3500 ppm, 3600 ppm, 3700 ppm, 3800 ppm, or 3900 ppm. The final concentration of steviol glycoside can be greater than 3000 ppm, 4000 ppm, 5000 ppm, 6000 ppm, 7000 ppm, 8000 ppm, or 9000 ppm. The final concentration of steviol glycoside can be greater than 1%, 2%, 3%, 4%, 5%, 6%, 7%, 8%, 9%, 10%, or higher.

In some aspects, the readily dissolvable steviol glycoside composition comprises an increased rate of solution in a primarily aqueous solution when compared to a steviol glycoside composition without a dissolution enhancer compound when a final concentration of dissolution enhancer compound is between 3000 ppm and 60000 ppm. The final concentration of dissolution enhancer compound can be greater than 100 ppm, 200 ppm, 300 ppm, 400 ppm, 500 ppm, 600 ppm, 700 ppm, 800 ppm, 900 ppm, or 1000 ppm. The final concentration of dissolution enhancer compound can be greater than 1100 ppm, 1200 ppm, 1300 ppm, 1400 ppm, 1500 ppm, 1600 ppm, 1700 ppm, 1800 ppm, or 1900 ppm. The final concentration of dissolution enhancer compound can be greater than 2100 ppm, 2200 ppm, 2300 ppm, 2400 ppm, 2500 ppm, 2600 ppm, 2700 ppm, 2800 ppm, or 2900 ppm. The final concentration of dissolution enhancer compound can be greater than 3100 ppm, 3200 ppm, 3300 ppm, 3400 ppm, 3500 ppm, 3600 ppm, 3700 ppm, 3800 ppm, or 3900 ppm. The final concentration of dissolution enhancer compound can be greater than 3000 ppm, 4000 ppm, 5000 ppm, 6000 ppm, 7000 ppm, 8000 ppm, or 9000 ppm. The final concentration of dissolution enhancer compound can be greater than 1%, 2%, 3%, 4%, 5%, 6%, 7%, 8%, 9%, 10%, or higher.

In some aspects, the readily dissolvable steviol glycoside composition comprises an increased rate of solution in a primarily aqueous solution when compared to a steviol glycoside composition without a dissolution enhancer compound when the dissolution is carried out at a temperature less than 5° C., 10° C., 15° C., 20° C., 25° C., 30° C., 35° C., 40° C., 45° C., 50° C., 55° C., 60° C., 65° C., 70° C., 75° C., 80° C., or 85° C. The dissolution can be carried out at between 5° C. and 65° C. The dissolution can be carried out between 20° C. and 65° C. The dissolution can be carried out at between 10° C. and 40° C. The dissolution can be carried out at between 15° C. and 30° C. The dissolution can be carried out at between 20° C. and 25° C. The dissolution can be carried out at about room temperature. The dissolution can be carried out at essentially room temperature.

In some aspects, the readily dissolvable steviol glycoside composition can dissolve completely. The readily dissolvable steviol glycoside composition can dissolve completely within 1, 2, 3, 4, 5, 6, 7, 8, 9, 10, 11, 12, 13, 14, 15, 20, 25, 30, 35, 40, 45, 50, 55 or 60 minutes. The readily dissolvable steviol glycoside composition can dissolve completely within 1, 2, or 3 hours.

In some aspects, this disclosure also relates to readily dissolvable steviol glycoside compositions with a high rate of solution. An example of a readily dissolvable steviol glycoside composition with a high rate of solution is a composition comprising an admixture of a steviol glycoside and a dissolution enhancer compound in an amount effective to increase dissolution of the steviol glycoside. As described above, the term a high rate of solution can refer to a readily dissolvable composition and/or a composition with a high rate of dissolution in certain solvents. A high rate of solution can also refer to a composition comprising instantaneous solubility in certain solvents. For example, a steviol glycoside composition with a high rate of solution can comprise a high rate of dissolution and/or instantaneous solubility in a primarily aqueous solution.

In some aspects, the compositions comprising steviol glycoside and dissolution enhancer compound can comprise any suitable additives including but not limited to buffering agent, acidulants, such as citric acid, antimicrobial agents, such as benzoic acid and sorbic acid (and salts thereof), natural colors, natural flavors, artificial flavors, artificial colors, and artificial sweeteners.

In some aspects, the compositions comprising steviol glycoside and dissolution enhancer compound can comprise less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

In some aspects, the admixture of a steviol glycoside and a dissolution enhancer compound can comprise any steviol glycoside described above. For example, the admixed steviol glycoside can include rebaudioside M, rebaudioside D, rebaudioside A, rebaudioside B, rebaudioside O, and/or rebaudioside N. The admixed steviol glycoside can be in a crystalline form. Likewise, the admixed dissolution enhancer compound can comprise any suitable dissolution enhancer compound described above. For example, the admixed dissolution enhancer compound can include caffeic acid, monocaffeoylquinic acids (e.g. chlorogenic acid, neochlorogenic acid, and cryptochlorogenic acid), and dicaffeoylquinic acids (e.g. 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid), and salts thereof. The admixed dissolution enhancer compound can be prepared from any suitable source, including yerba mate, stevia, globe artichoke, and/or green coffee bean.

In some aspects, the admixture of the steviol glycoside and a dissolution enhancer compound can comprise any suitable ratio effective to increase dissolution of the steviol glycoside, as described above. For example, the amount of admixed dissolution enhancer compound effective to increase dissolution of the steviol glycoside can be an amount such that the dissolution enhancer compound comprises a ratio by weight of steviol glycoside to dissolution enhancer of about 1:0.1, 1:0.3, 1:0.5, 1:1, 1:2, 1:3, 1:4, 1:5, 1:6, 1:7, 1:8, 1:9, or 1:10 by weight.

The admixture of the steviol glycoside and a dissolution enhancer compound can be prepared by any suitable means to result in a composition with a high rate of solution. For example, dry steviol glycoside and dry dissolution enhancer compound can be combined to form a dry admixture. Likewise, a solution of steviol glycoside and dissolution enhancer compound can prepared and then dried to prepare the admixture. The admixture can comprise any other suitable ingredients. For example, the admixture can comprise a buffering system (e.g., a citrate/phosphate buffer). In some aspects, the buffering system can provide a pH of 0, 1, 2, 3, 4, 5, or 6. The pH can be between 1 and 6. The pH can be between 1.5 and 4.

In some aspects, the admixture of the steviol glycoside and the dissolution enhancer compound comprises an increased rate of dissolution in a primarily aqueous solution when compared to a steviol glycoside composition without a dissolution enhancer compound. The dissolution can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the dissolution can be increased by 1, 2, 3, 4, 5, 6, 7, 8, 9, or 10 times or more when compared to a composition without a dissolution enhancer compound.

In some aspects, the admixture of the steviol glycoside and the dissolution enhancer compound comprises an increased rate of solution in a primarily aqueous solution when compared to a steviol glycoside composition without a dissolution enhancer compound. The rate of solution can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the rate of solution can be increased by 1, 2, 3, 4, 5, 6, 7, 8, 9, or 10 times or more when compared to a composition without a dissolution enhancer compound.

In some aspects, the admixture of the steviol glycoside and the dissolution enhancer compound comprises an instantaneous solubility in a primarily aqueous solution when compared to a steviol glycoside composition without a dissolution enhancer compound. The instantaneous solubility can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the instantaneous solubility can be increased by 1, 2, 3, 4, 5, 6, 7, 8, 9, or 10 times or more when compared to a composition without a dissolution enhancer compound.

In some aspects, the admixture of the steviol glycoside and the dissolution enhancer compound comprises less than 1% stevioside. The admixture of the steviol glycoside and the dissolution enhancer compound can comprise less than 1% rebaudioside B. The admixture of the steviol glycoside and the dissolution enhancer compound can comprise less than 1% steviolbioside. The admixture of the steviol glycoside and the dissolution enhancer compound can comprise less than 1% 13-SMG. In other aspects, the admixture of the steviol glycoside and the dissolution enhancer compound comprises less than one or more of 1% stevioside, 1% rebaudioside B, 1% steviolbioside, and 1% 13-SMG.

In some aspects, the admixture of the steviol glycoside and the dissolution enhancer compound comprises an increased rate of solution in a primarily aqueous solution when compared to a steviol glycoside composition without a dissolution enhancer compound when a final concentration of steviol glycoside is between 3000 ppm and 60000 ppm. The final concentration of steviol glycoside can be greater than 100 ppm, 200 ppm, 300 ppm, 400 ppm, 500 ppm, 600 ppm, 700 ppm, 800 ppm, 900 ppm, or 1000 ppm. The final concentration of steviol glycoside can be greater than 1100 ppm, 1200 ppm, 1300 ppm, 1400 ppm, 1500 ppm, 1600 ppm, 1700 ppm, 1800 ppm, or 1900 ppm. The final concentration of steviol glycoside can be greater than 2100 ppm, 2200 ppm, 2300 ppm, 2400 ppm, 2500 ppm, 2600 ppm, 2700 ppm, 2800 ppm, or 2900 ppm. The final concentration of steviol glycoside can be greater than 3100 ppm, 3200 ppm, 3300 ppm, 3400 ppm, 3500 ppm, 3600 ppm, 3700 ppm, 3800 ppm, or 3900 ppm. The final concentration of steviol glycoside can be greater than 3000 ppm, 4000 ppm, 5000 ppm, 6000 ppm, 7000 ppm, 8000 ppm, or 9000 ppm. The final concentration of steviol glycoside can be greater than 1%, 2%, 3%, 4%, 5%, 6%, 7%, 8%, 9%, 10%, or higher.

In some aspects, the admixture of the steviol glycoside and the dissolution enhancer compound comprises an increased rate of solution in a primarily aqueous solution when compared to a steviol glycoside composition without a dissolution enhancer compound when a final concentration of dissolution enhancer compound is between 3000 ppm and 60000 ppm. The final concentration of dissolution enhancer compound can be greater than 100 ppm, 200 ppm, 300 ppm, 400 ppm, 500 ppm, 600 ppm, 700 ppm, 800 ppm, 900 ppm, or 1000 ppm. The final concentration of dissolution enhancer compound can be greater than 1100 ppm, 1200 ppm, 1300 ppm, 1400 ppm, 1500 ppm, 1600 ppm, 1700 ppm, 1800 ppm, or 1900 ppm. The final concentration of dissolution enhancer compound can be greater than 2100 ppm, 2200 ppm, 2300 ppm, 2400 ppm, 2500 ppm, 2600 ppm, 2700 ppm, 2800 ppm, or 2900 ppm. The final concentration of dissolution enhancer compound can be greater than 3100 ppm, 3200 ppm, 3300 ppm, 3400 ppm, 3500 ppm, 3600 ppm, 3700 ppm, 3800 ppm, or 3900 ppm. The final concentration of dissolution enhancer compound can be greater than 3000 ppm, 4000 ppm, 5000 ppm, 6000 ppm, 7000 ppm, 8000 ppm, or 9000 ppm. The final concentration of dissolution enhancer compound can be greater than 1%, 2%, 3%, 4%, 5%, 6%, 7%, 8%, 9%, 10%, or higher.

In some aspects, the admixture of the steviol glycoside and the dissolution enhancer compound comprises an increased rate of solution in a primarily aqueous solution when compared to a steviol glycoside composition without a dissolution enhancer compound when the dissolution is carried out at a temperature less than 5° C., 10° C., 15° C., 20° C., 25° C., 30° C., 35° C., 40° C., 45° C., 50° C., 55° C., 60° C., 65° C., 70° C., 75° C., 80° C., or 85° C. The dissolution can be carried out at between 5° C. and 65° C. The dissolution can be carried out between 20° C. and 65° C. The dissolution can be carried out at between 10° C. and 40° C. The dissolution can be carried out at between 15° C. and 30° C. The dissolution can be carried out at between 20° C. and 25° C. The dissolution can be carried out at about room temperature. The dissolution can be carried out at essentially room temperature.

In some aspects, the admixture of the steviol glycoside and the dissolution enhancer compound can dissolve completely. The admixture of the steviol glycoside and the dissolution enhancer compound can dissolve completely within 1, 2, 3, 4, 5, 6, 7, 8, 9, 10, 11, 12, 13, 14, 15, 20, 25, 30, 35, 40, 45, 50, 55 or 60 minutes. The admixture of the steviol glycoside and the dissolution enhancer compound can dissolve completely within 1, 2, or 3 hours.

In some aspects, this disclosure also relates to methods of increasing dissolution of crystalline steviol glycoside. An example of a method for increasing dissolution of a crystalline steviol glycoside, comprises contacting a crystalline steviol glycoside and a dissolution enhancer compound in an amount effective to increase dissolution of the steviol glycoside with a primarily aqueous solution.

In some aspects, the crystalline steviol glycoside can comprise any steviol glycoside described above. For example, the steviol glycoside can include crystalline forms of one or more of rebaudioside M, rebaudioside D, rebaudioside A, rebaudioside B, rebaudioside O, rebaudioside N, and/or stevioside. The dissolution enhancer compound can comprise any suitable dissolution enhancer compound described above. For example, the dissolution enhancer compound can include caffeic acid, monocaffeoylquinic acids (e.g. chlorogenic acid, neochlorogenic acid, and cryptochlorogenic acid), and dicaffeoylquinic acids (e.g. 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid), and salts thereof. The dissolution enhancer compound can be prepared from any suitable source, including yerba mate, *stevia*, globe artichoke, and/or green coffee.

In some aspects, the crystalline steviol glycoside and dissolution enhancer compound can comprise any suitable ratio, as described above. For example, the amount of admixed dissolution enhancer compound effective to increase dissolution of the steviol glycoside can be an amount such that the dissolution enhancer comprises a ratio by weight of dissolution enhancer compound to steviol glycoside of about 1:0.1, 1:0.3, 1:0.5, 1:1, 1:2, 1:3, 1:4, 1:5, 1:6, 1:7, 1:8, 1:9, or 1:10 by weight. the ratio of dissolution enhancer compound to steviol glycoside can be from about 0.1:1 to 10:1. In some aspects, the ratio of dissolution enhancer compound to steviol glycoside can be in the range of about 0.1:1 to 5:1, about 0.5:1 to 4:1, or about 1:1 to 3:1. In other aspects, the ratio of dissolution enhancer compound to steviol glycoside is about 0.1:1, 0.5:1, 1:1, 2:1, 3:1, 4:1, 5:1, 6:1, 7:1, 8:1, 9:1, or 10:1.

In some aspects, the rate of dissolution is increased in a primarily aqueous solution when compared to a steviol glycoside composition without a dissolution enhancer compound. The dissolution rate can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the dissolution rate can be increased by 1, 2, 3, 4, 5, 6, 7, 8, 9, or 10 times or more when compared to a composition without a dissolution enhancer compound.

In some aspects, the increased rate of dissolution corresponds to an increased rate of solution in a primarily aqueous solution when compared to a steviol glycoside composition without a dissolution enhancer compound. The rate of solution can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the rate of solution can be increased by 1, 2, 3, 4, 5, 6, 7, 8, 9, or 10 times or more when compared to a composition without a dissolution enhancer compound. In some aspects, the increased rate of dissolution corresponds to an increase in instantaneous solubility in a primarily aqueous solution when compared to a steviol glycoside composition without a dissolution enhancer compound. The instantaneous solubility can be increased by at least 5%, 10%, 15%, 20%, 25%, 30%, 35%, 40%, 45%, 50%, 55%, 60%, 65%, 70%, 75%, 80%, 85%, 90%, 95%, or 100% or more when compared to a composition without a dissolution enhancer compound. In other aspects, the instantaneous solubility can be increased by 1, 2, 3, 4, 5, 6, 7, 8, 9, or 10 times or more when compared to a composition without a dissolution enhancer compound.

In some aspects, the primarily aqueous solution in which the crystalline steviol glycoside is dissolved comprises primarily water. The primarily aqueous solution can also comprise less than 1%, 5%, 10%, 15%, 20%, 30%, 40%, 45%, 50%, 55%, 60%, 65%, 70%, 80%, or 90%, or about 40% to 65%, or about 50% to 55%, or about 55% of C1-C4 alcohol (e.g., methanol, ethanol, propanol, butanol, etc.). The primarily aqueous solution can be substantially free of C1-C4 alcohols. In other aspects, the primarily aqueous solution is essentially free of C1-C4 alcohols.

In some aspects, the primarily aqueous solution in which the crystalline steviol glycoside is dissolved comprises less than 1% stevioside. The primarily aqueous solution can comprise less than 1% rebaudioside B. The primarily aqueous solution can comprise less than 1% steviolbioside. The primarily aqueous solution can comprise less than 1% 13-SMG. In other aspects, the primarily aqueous solution comprises less than one or more of 1% stevioside, 1% rebaudioside B, 1% steviolbioside, and 1% 13-SMG.

In some aspects, the primarily aqueous solution in which the crystalline steviol glycoside is dissolved has any suitable pH. The primarily aqueous solution can also comprise a pH of 0, 1, 2, 3, 4, 5, or 6. The primarily aqueous solution can comprise a pH of between 0 and 7. The primarily aqueous solution can comprise a pH of between 1 and 6. The primarily aqueous solution can comprise a pH of between 1.5 and 4.

In some aspects, the method for increasing dissolution of a crystalline steviol glycoside comprises an increased rate of solution in a primarily aqueous solution when compared to a steviol glycoside composition without a dissolution enhancer compound when a final concentration of steviol glycoside is between 3000 ppm and 60000 ppm. The final concentration of steviol glycoside can be greater than 100 ppm, 200 ppm, 300 ppm, 400 ppm, 500 ppm, 600 ppm, 700 ppm, 800 ppm, 900 ppm, or 1000 ppm. The final concentration of steviol glycoside can be greater than 1100 ppm, 1200 ppm, 1300 ppm, 1400 ppm, 1500 ppm, 1600 ppm, 1700 ppm, 1800 ppm, or 1900 ppm. The final concentration of steviol glycoside can be greater than 2100 ppm, 2200 ppm, 2300 ppm, 2400 ppm, 2500 ppm, 2600 ppm, 2700 ppm, 2800 ppm, or 2900 ppm. The final concentration of steviol glycoside can be greater than 3100 ppm, 3200 ppm, 3300 ppm, 3400 ppm, 3500 ppm, 3600 ppm, 3700 ppm, 3800 ppm, or 3900 ppm. The final concentration of steviol glycoside can be greater than 3000 ppm, 4000 ppm, 5000 ppm, 6000 ppm, 7000 ppm, 8000 ppm, or 9000 ppm. The final concentration of steviol glycoside can be greater than 1%, 2%, 3%, 4%, 5%, 6%, 7%, 8%, 9%, 10%, or higher.

In some aspects, the method for increasing dissolution of a crystalline steviol glycoside comprises an increased rate of solution in a primarily aqueous solution when compared to a steviol glycoside composition without a dissolution enhancer compound when a final concentration of dissolution enhancer compound is between 3000 ppm and 60000 ppm. The final concentration of dissolution enhancer compound can be greater than 100 ppm, 200 ppm, 300 ppm, 400 ppm, 500 ppm, 600 ppm, 700 ppm, 800 ppm, 900 ppm, or 1000 ppm. The final concentration of dissolution enhancer compound can be greater than 1100 ppm, 1200 ppm, 1300 ppm, 1400 ppm, 1500 ppm, 1600 ppm, 1700 ppm, 1800 ppm, or 1900 ppm. The final concentration of dissolution enhancer compound can be greater than 2100 ppm, 2200 ppm, 2300 ppm, 2400 ppm, 2500 ppm, 2600 ppm, 2700 ppm, 2800 ppm, or 2900 ppm. The final concentration of dissolution enhancer compound can be greater than 3100 ppm, 3200 ppm, 3300 ppm, 3400 ppm, 3500 ppm, 3600 ppm, 3700 ppm, 3800 ppm, or 3900 ppm. The final concentration of dissolution enhancer compound can be greater than 3000 ppm, 4000 ppm, 5000 ppm, 6000 ppm, 7000 ppm, 8000 ppm, or 9000 ppm. The final concentration of dissolution enhancer compound can be greater than 1%, 2%, 3%, 4%, 5%, 6%, 7%, 8%, 9%, 10%, or higher.

In some aspects, the method for increasing dissolution of a crystalline steviol glycoside is carried out at a temperature less than 5° C., 10° C., 15° C., 20° C., 25° C., 30° C., 35° C., 40° C., 45° C., 50° C., 55° C., 60° C., 65° C., 70° C., 75° C., 80° C., or 85° C. The method for increasing dissolution of a crystalline steviol glycoside can be carried out at between 5° C. and 65° C. The dissolution can be carried out between 20° C. and 65° C. The dissolution can be carried out at between 10° C. and 40° C. The method for increasing dissolution of a crystalline steviol glycoside can be carried out at between 15° C. and 30° C. The method for increasing dissolution of a crystalline steviol glycoside can be carried out at between 20° C. and 25° C. The method for increasing dissolution of a crystalline steviol glycoside can be carried out at about room temperature. The method for increasing dissolution of a crystalline steviol glycoside can be carried out at essentially room temperature.

In some aspects, the crystalline steviol glycoside composition can dissolve completely. The crystalline steviol glycoside composition can dissolve completely within 1, 2, 3, 4, 5, 6, 7, 8, 9, 10, 11, 12, 13, 14, 15, 20, 25, 30, 35, 40, 45, 50, 55 or 60 minutes. The crystalline steviol glycoside composition can dissolve completely within 1, 2, or 3 hours.

In some aspects, this disclosure also relates to methods of preparing concentrated steviol glycoside solutions from crystalline steviol glycoside. An example of a method of preparing a concentrated steviol glycoside solution comprises dissolving a crystalline steviol glycoside and a dissolution enhancer compound in water, wherein a final concentration of the concentrated steviol glycoside solution is greater than 0.15% (wt), 0.2% (wt), 0.25% (wt), 0.3% (wt), 0.4% (wt), 0.5% (wt), 1% (wt), 3% (wt), 5% (wt), 10% (wt), 20% (wt), or greater.

In some aspects, the crystalline steviol glycoside can comprise any steviol glycoside described above. For example, the steviol glycoside can include crystalline forms of one or more of rebaudioside M, rebaudioside D, rebaudioside A, rebaudioside B, rebaudioside O, rebaudioside N, and/or stevioside. The dissolution enhancer compound can comprise any suitable dissolution enhancer compound described above. For example, the dissolution enhancer compound can include caffeic acid, monocaffeoylquinic acids (e.g. chlorogenic acid, neochlorogenic acid, and cryptochlorogenic acid), and dicaffeoylquinic acids (e.g. 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid), and salts thereof. The dissolution enhancer compound can be prepared from any suitable source, including yerba mate, *stevia*, globe artichoke, and/or green coffee.

In some aspects, the crystalline steviol glycoside and a dissolution enhancer compound can comprise any suitable ratio, as described above. For example, the ratio of dissolution enhancer compound to steviol glycoside can be from about 0.1:1 to 10:1. In some aspects, the ratio of dissolution enhancer compound to steviol glycoside can be in the range of about 0.1:1 to 5:1, about 0.5:1 to 4:1, or about 1:1 to 3:1. In other aspects, the ratio of dissolution enhancer compound to steviol glycoside is about 0.1:1, 0.3:1, 0.5:1, 0.7:1, 1:1, 2:1, 3:1, 4:1, 5:1, 6:1, 7:1, 8:1, 9:1, or 10:1.

In some aspects, the primarily aqueous solution in which the crystalline steviol glycoside is dissolved comprises primarily water. The primarily aqueous solution can also comprise less than 1%, 5%, 10%, 15%, 20%, 30%, 40%, 45%, 50%, 55%, 60%, 65%, 70%, 80%, or 90%, or about 40% to 65%, or about 50% to 55%, or about 55% of C1-C4 alcohol (e.g., methanol, ethanol, propanol, butanol, etc.). The primarily aqueous solution can be substantially free of C1-C4 alcohols. In other aspects, the primarily aqueous solution is essentially free of C1-C4 alcohols.

In some aspects, the primarily aqueous solution in which the crystalline steviol glycoside is dissolved comprises less than 1% stevioside. The primarily aqueous solution can comprise less than 1% rebaudioside B. The primarily aqueous solution can comprise less than 1% steviolbioside. The primarily aqueous solution can comprise less than 1% 13-SMG. In other aspects, the primarily aqueous solution comprises less than one or more of 1% stevioside, 1% rebaudioside B, 1% steviolbioside, and 1% 13-SMG.

In some aspects, the primarily aqueous solution in which the crystalline steviol glycoside is dissolved has any suitable pH. The primarily aqueous solution can also comprise a pH of 0, 1, 2, 3, 4, 5, or 6. The primarily aqueous solution can comprise a pH of between 0 and 7. The primarily aqueous solution can comprise a pH of between 1 and 6. The primarily aqueous solution can comprise a pH of between 1.5 and 4.

In some aspects, the concentrated steviol glycoside solution comprises a final concentration of steviol glycoside is between 3000 ppm and 60000 ppm. The final concentration of steviol glycoside can be greater than 100 ppm, 200 ppm, 300 ppm, 400 ppm, 500 ppm, 600 ppm, 700 ppm, 800 ppm, 900 ppm, or 1000 ppm. The final concentration of steviol glycoside can be greater than 1100 ppm, 1200 ppm, 1300 ppm, 1400 ppm, 1500 ppm, 1600 ppm, 1700 ppm, 1800 ppm, or 1900 ppm. The final concentration of steviol glycoside can be greater than 2100 ppm, 2200 ppm, 2300 ppm, 2400 ppm, 2500 ppm, 2600 ppm, 2700 ppm, 2800 ppm, or 2900 ppm. The final concentration of steviol glycoside can be greater than 3100 ppm, 3200 ppm, 3300 ppm, 3400 ppm, 3500 ppm, 3600 ppm, 3700 ppm, 3800 ppm, or 3900 ppm. The final concentration of steviol glycoside can be greater than 3000 ppm, 4000 ppm, 5000 ppm, 6000 ppm, 7000 ppm, 8000 ppm, or 9000 ppm. The final concentration of steviol glycoside can be greater than 1%, 2%, 3%, 4%, 5%, 6%, 7%, 8%, 9%, 10%, or higher.

In some aspects, the concentrated steviol glycoside solution comprises a final concentration of dissolution enhancer compound is between 3000 ppm and 60000 ppm. The final concentration of dissolution enhancer compound can be greater than 100 ppm, 200 ppm, 300 ppm, 400 ppm, 500 ppm, 600 ppm, 700 ppm, 800 ppm, 900 ppm, or 1000 ppm. The final concentration of dissolution enhancer compound can be greater than 1100 ppm, 1200 ppm, 1300 ppm, 1400 ppm, 1500 ppm, 1600 ppm, 1700 ppm, 1800 ppm, or 1900 ppm. The final concentration of dissolution enhancer compound can be greater than 2100 ppm, 2200 ppm, 2300 ppm, 2400 ppm, 2500 ppm, 2600 ppm, 2700 ppm, 2800 ppm, or 2900 ppm. The final concentration of dissolution enhancer compound can be greater than 3100 ppm, 3200 ppm, 3300 ppm, 3400 ppm, 3500 ppm, 3600 ppm, 3700 ppm, 3800 ppm, or 3900 ppm. The final concentration of dissolution enhancer compound can be greater than 3000 ppm, 4000 ppm, 5000 ppm, 6000 ppm, 7000 ppm, 8000 ppm, or 9000 ppm. The final concentration of dissolution enhancer compound can be greater than 1%, 2%, 3%, 4%, 5%, 6%, 7%, 8%, 9%, 10%, or higher.

In some aspects, the concentrated steviol glycoside solution is prepared at a temperature less than 5° C., 10° C., 15° C., 20° C., 25° C., 30° C., 35° C., 40° C., 45° C., 50° C., 55° C., 60° C., 65° C., 70° C., 75° C., 80° C., or 85° C. The concentrated steviol glycoside solution is prepared at between 5° C. and 65° C. The dissolution can be carried out between 20° C. and 65° C. The concentrated steviol glycoside solution is prepared at between 10° C. and 40° C. The concentrated steviol glycoside solution is prepared at between 15° C. and 30° C. The concentrated steviol glycoside solution is prepared at between 20° C. and 25° C. The concentrated steviol glycoside solution can be prepared at about room temperature. The concentrated steviol glycoside solution can be prepared at essentially room temperature.

In some aspects, the crystalline steviol glycoside composition can dissolve completely to make the concentrated steviol glycoside solution. The crystalline steviol glycoside composition can dissolve completely within 1, 2, 3, 4, 5, 6, 7, 8, 9, 10, 11, 12, 13, 14, 15, 20, 25, 30, 35, 40, 45, 50, 55 or 60 minutes. The crystalline steviol glycoside composition can dissolve completely within 1, 2, or 3 hours.

In some aspects, this disclosure also relates to methods of preparing a beverage concentrate from crystalline steviol glycoside. An example of a method for preparing a beverage concentrate comprises contacting a crystalline steviol glycoside, a dissolution enhancer compound, and water.

In some aspects, the crystalline steviol glycoside can comprise any steviol glycoside described above. For example, the steviol glycoside can include crystalline forms of one or more of rebaudioside M, rebaudioside D, rebaudioside A, rebaudioside B, rebaudioside N, and/or stevioside. The dissolution enhancer compound can comprise any suitable dissolution enhancer compound described above. For example, the dissolution enhancer compound can include caffeic acid, monocaffeoylquinic acids (e.g. chlorogenic acid, neochlorogenic acid, and cryptochlorogenic acid), and dicaffeoylquinic acids (e.g. 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid), and salts thereof. The dissolution enhancer compound can be prepared from any suitable source, including *stevia* and/or yerba mate.

In some aspects, the crystalline steviol glycoside and a dissolution enhancer compound can comprise any suitable ratio, as described above. For example, the ratio of dissolution enhancer compound to steviol glycoside can be from about 0.1:1 to 10:1. In some aspects, the ratio of dissolution enhancer compound to steviol glycoside can be in the range of about 0.1:1 to 5:1, about 0.5:1 to 4:1, or about 1:1 to 3:1. In other aspects, the ratio of dissolution enhancer compound to steviol glycoside is about 0.1:1, 0.3:1, 0.5:1, 0.7:1, 1:1, 2:1, 3:1, 4:1, 5:1, 6:1, 7:1, 8:1, 9:1, or 10:1.

In some aspects, the beverage concentrate comprises less than 1%, 5%, 10%, 15%, 20%, 30%, 40%, 45%, 50%, 55%, 60%, 65%, 70%, 80%, or 90%, or about 40% to 65%, or about 50% to 55%, or about 55% of C1-C4 alcohol (e.g., methanol, ethanol, propanol, butanol, etc.). The beverage concentrate can be substantially free of C1-C4 alcohols. In other aspects, the beverage concentrate is essentially free of C1-C4 alcohols. In other aspects, the beverage concentrate in which the crystalline steviol glycoside is dissolved comprises less than 1% stevioside. The water can comprise less than 1% rebaudioside B. The beverage concentrate can comprise less than 1% rebaudioside F. The beverage concentrate can comprise less than 1% rebaudioside C. In other aspects, the beverage concentrate comprises less than one or more of 1% stevioside, 1% rebaudioside B, 1% rebaudioside F, 1% steviolbioside, 1% 13-SMG, and 1% rebaudioside C.

In some aspects, the beverage concentrate comprises a final concentration of steviol glycoside is between 3000 ppm and 60000 ppm. The final concentration of steviol glycoside can be greater than 100 ppm, 200 ppm, 300 ppm, 400 ppm, 500 ppm, 600 ppm, 700 ppm, 800 ppm, 900 ppm, or 1000 ppm. The final concentration of steviol glycoside can be greater than 1100 ppm, 1200 ppm, 1300 ppm, 1400 ppm, 1500 ppm, 1600 ppm, 1700 ppm, 1800 ppm, or 1900 ppm. The final concentration of steviol glycoside can be greater than 2100 ppm, 2200 ppm, 2300 ppm, 2400 ppm, 2500 ppm, 2600 ppm, 2700 ppm, 2800 ppm, or 2900 ppm. The final concentration of steviol glycoside can be greater than 3100 ppm, 3200 ppm, 3300 ppm, 3400 ppm, 3500 ppm, 3600 ppm, 3700 ppm, 3800 ppm, or 3900 ppm. The final concentration of steviol glycoside can be greater than 3000 ppm, 4000 ppm, 5000 ppm, 6000 ppm, 7000 ppm, 8000 ppm, or 9000 ppm. The final concentration of steviol glycoside can be greater than 1%, 2%, 3%, 4%, 5%, 6%, 7%, 8%, 9%, 10%, or higher.

In some aspects, the beverage concentrate comprises a final concentration of dissolution enhancer compound is between 3000 ppm and 60000 ppm. The final concentration of dissolution enhancer compound can be greater than 100 ppm, 200 ppm, 300 ppm, 400 ppm, 500 ppm, 600 ppm, 700 ppm, 800 ppm, 900 ppm, or 1000 ppm. The final concentration of dissolution enhancer compound can be greater than 1100 ppm, 1200 ppm, 1300 ppm, 1400 ppm, 1500 ppm, 1600 ppm, 1700 ppm, 1800 ppm, or 1900 ppm. The final concentration of dissolution enhancer compound can be greater than 2100 ppm, 2200 ppm, 2300 ppm, 2400 ppm, 2500 ppm, 2600 ppm, 2700 ppm, 2800 ppm, or 2900 ppm. The final concentration of dissolution enhancer compound can be greater than 3100 ppm, 3200 ppm, 3300 ppm, 3400 ppm, 3500 ppm, 3600 ppm, 3700 ppm, 3800 ppm, or 3900 ppm. The final concentration of dissolution enhancer compound can be greater than 3000 ppm, 4000 ppm, 5000 ppm, 6000 ppm, 7000 ppm, 8000 ppm, or 9000 ppm. The final concentration of dissolution enhancer compound can be greater than 1%, 2%, 3%, 4%, 5%, 6%, 7%, 8%, 9%, 10%, or higher.

In some aspects, the beverage concentrate is prepared at a temperature less than 5° C., 10° C., 15° C., 20° C., 25° C., 30° C., 35° C., 40° C., 45° C., 50° C., 55° C., 60° C., 65° C., 70° C., 75° C., 80° C., or 85° C. The beverage concentrate is prepared at between 5° C. and 65° C. The dissolution can be carried out between 20° C. and 65° C. The beverage concentrate is prepared at between 10° C. and 40° C. The beverage concentrate is prepared at between 15° C. and 30° C. The beverage concentrate is prepared at between 20° C. and 25° C. The beverage concentrate can be prepared at about room temperature. The beverage concentrate can be prepared at essentially room temperature.

In some aspects, the crystalline steviol glycoside composition can dissolve completely to make the beverage concentrate. The crystalline steviol glycoside composition can dissolve completely within 1, 2, 3, 4, 5, 6, 7, 8, 9, 10, 11, 12, 13, 14, 15, 20, 25, 30, 35, 40, 45, 50, 55 or 60 minutes. The crystalline steviol glycoside can dissolve completely within 1, 2, or 3 hours.

The beverage concentrate can further comprise a buffer (e.g., a citrate/phosphate buffer). In some aspects, the buffer can provide a pH of 0, 1, 2, 3, 4, 5, or 6. The pH can be between 1 and 6. The pH can be between 1.5 and 4.

In some aspects, the beverage concentrate can further comprise any suitable flavor and/or color. In some aspects, the beverage concentrate can further comprise any suitable ingredient including buffering agent, acidulants, such as citric acid, antimicrobial agents, such as benzoic acid and sorbic acid (and salts thereof), natural colors, natural flavors, artificial flavors, artificial colors, and artificial sweeteners.

EXAMPLES

The following examples are provided to illustrate the disclosure, but are not intended to limit the scope thereof. All parts and percentages are by weight unless otherwise indicated.

Example 1

A series of dissolution assays were carried out on the dissolution of a steviol glycoside blend with and without dissolution enhancer compound. The dissolution assays were performed in an acidic citrate/phosphate buffer system similar to that of a carbonated soda beverage concentrate (or throw syrup). One steviol glycoside blend comprised primarily rebaudioside D and rebaudioside M (RM80, >80% (wt) rebaudioside M). Another steviol glycoside blend comprised a 95% rebaudioside A blend (RA95). The dissolution enhancer compounds were prepared from stevia leaf and also from yerba mate.

An aqueous solution of citrate/phosphate buffer (about 4 g/L) was prepared and adjusted to pH 2.5. Separate capped glass vials were prepared, 10 mL of the aqueous buffered solution was aliquoted into each vial, and a magnetic stir bar added to each vial. Dry powdered samples of steviol glycoside blends were added to some vials under magnetic stirring. Dry powdered samples of steviol glycoside blends along with dry powdered samples of dissolution enhancer compounds were added to other vials under magnetic stirring. Each vial was monitored over time for dissolution under magnetic stirring and the results recorded by video or still image.

A control vial was prepared with 10 mL of the aqueous buffered solution as described above. A dry powdered sample of the RM80 corresponding to a final steviol glycoside concentration of 3000 ppm was added to the aqueous buffered solution under magnetic stirring at room temperature. Magnetic stirring was continued and dissolution monitored over time. The initially clear aqueous buffered solution became cloudy upon addition of the RM80. At 1 minute after addition of the RM80 the aqueous buffered solution remained cloudy. At 10 minutes after addition of the RM80 the aqueous buffered solution remained cloudy. At 45 minutes after addition of the RM80 the aqueous buffered solution remained cloudy. At 1440 minutes after addition of the RM80 the aqueous buffered solution remained cloudy. Table 1 tabulates the observations of the control vial at 0 minutes, 1 minute, 10 minutes, 45 minutes, 60 minutes, 120 minutes, 300 minutes, and 1440 minutes, respectively.

TABLE 1

Observations of control vial over time

| Time (min) | Observation |
| --- | --- |
| 0 | Cloudy |
| 1 | Cloudy |
| 10 | Cloudy |
| 45 | Cloudy |
| 60 | Cloudy |
| 120 | Cloudy |
| 300 | Cloudy |
| 1440 | Cloudy |

Table 1 shows that the RM80 added to the aqueous buffered solution remained cloudy over the course of the monitoring. This control vial experiment showed that the RM80 at a final steviol glycoside concentration of 3000 ppm did not dissolve completely in the aqueous buffered solution.

Example 2

A vial was prepared with 10 mL of the aqueous buffered solution as described above. A dry powdered sample of the RM80 corresponding to a final steviol glycoside concentration of 3000 ppm was added to the aqueous buffered solution under magnetic stirring at room temperature. A dry powdered sample of the dissolution enhancer compound prepared from stevia corresponding to a final concentration of 3000 ppm was also added to the aqueous buffered solution under magnetic stirring at room temperature. Magnetic stirring was continued and dissolution monitored over time. The initially clear aqueous buffered solution became cloudy upon addition of the RM80. At 1 minute after addition of the RM80 the aqueous buffered solution became slightly less cloudy. At 3 minutes after addition of the RM80 the aqueous buffered solution became less cloudy. At 11 minutes after addition of the RM80 the aqueous buffered solution was clear with a few steviol glycoside crystals remaining. At 15 minutes after addition of the RM80 the aqueous buffered solution was completely clear with no steviol glycoside crystals remaining. Table 2 tabulates observations of the vial at 0 minutes, 1 minute, 3 minutes, 11 minutes, 15 minutes, 60 minutes, and 1440 minutes, respectively.

TABLE 2

Observations of test vial over time

| Time (min) | Observation |
| --- | --- |
| 0 | Cloudy |
| 1 | Slightly less cloudy |
| 3 | Less cloudy |

TABLE 2-continued

Observations of test vial over time

| Time (min) | Observation |
| --- | --- |
| 11 | Clear with few remaining steviol glycoside crystals |
| 15 | Completely clear |
| 60 | Completely clear |
| 1440 | Completely clear |

Table 2 shows that the RM80 added to the aqueous buffered solution with the dissolution enhancer compounds dissolved completely over the course of the monitoring. This experiment showed that the combination of the RM80 at a final steviol glycoside concentration of 3000 ppm and the dissolution enhancer compound from stevia at a final concentration of 3000 was able to readily dissolve in the aqueous buffered solution Example 3

A vial was prepared with 10 mL of the aqueous buffered solution as described above. A dry powdered sample of the RM80 corresponding to a final steviol glycoside concentration of 5000 ppm was added to the aqueous buffered solution under magnetic stirring at room temperature. A dry powdered sample of the dissolution enhancer compound prepared from stevia corresponding to a final concentration of 5000 ppm was also added to the aqueous buffered solution under magnetic stirring at room temperature. Magnetic stirring was continued and dissolution monitored over time. The initially clear aqueous buffered solution became cloudy upon addition of the RM80. At 10 minutes after addition of the RM80 the aqueous buffered solution became less cloudy. At 2 hours after addition of the RM80 the aqueous buffered solution was completely clear with no steviol glycoside crystals remaining. Table 3 lists observations of the test vial at 0 minutes, 10 minutes, 2 hours, and 24 hours, respectively.

TABLE 3

| Time (min) | Observation |
| --- | --- |
| 0 | Cloudy |
| 10 | Less cloudy |
| 120 | Completely clear |
| 1440 | Completely clear |

Table 3 shows that the RM80 added to the aqueous buffered solution with the dissolution enhancer compounds dissolved completely over the course of the monitoring. This experiment showed that the combination of the RM80 at a final steviol glycoside concentration of 5000 ppm and the dissolution enhancer compound from stevia at a final concentration of 5000 was able to dissolve completely in the aqueous buffered solution.

Example 4

A vial was prepared with 10 mL of the aqueous buffered solution as described above. A dry powdered sample of the RM80 corresponding to a final steviol glycoside concentration of 3000 ppm was added to the aqueous buffered solution under magnetic stirring at room temperature. A dry powdered sample of the dissolution enhancer compound prepared from yerba mate corresponding to a final concentration of 3000 ppm was also added to the aqueous buffered solution under magnetic stirring at room temperature. Magnetic stirring was continued and dissolution monitored over time. The initially clear aqueous buffered solution became cloudy upon addition of the RM80. At 5 minutes after addition of the RM80 the aqueous buffered solution became less cloudy. At 15 minutes after addition of the RM80 the aqueous buffered solution was less cloudy with some steviol glycoside crystals remaining. At 2 hours after addition of the RM80 the aqueous buffered solution was completely clear with no steviol glycoside crystals remaining. Table 4 shows observations of the test vial at 0 minutes, 5 minutes, 15 minutes, 2 hours, and 24 hours respectively.

TABLE 4

| Time (min) | Observation |
| --- | --- |
| 0 | Cloudy |
| 5 | Less cloudy |
| 15 | Less cloudy with some steviol glycoside crystals remaining |
| 120 | Completely clear |
| 1440 | Completely clear |

The RM80 added to the aqueous buffered solution with the dissolution enhancer compounds dissolved completely over the course of the monitoring. This experiment showed that the combination of the RM80 at a final steviol glycoside concentration of 3000 ppm and the dissolution enhancer compound from yerba mate at a final concentration of 3000 ppm was able to dissolve completely in the aqueous buffered solution.

Example 5

A vial was prepared with 10 mL of the aqueous buffered solution at pH 4 (citrate buffer, about 4 g/L). A dry powdered sample of the dissolution enhancer compound prepared from *stevia* and corresponding to a final concentration of 60000 ppm (6%) was added to the aqueous buffered solution at room temperature and the vial was capped and vortexed until the solubility enhancer dissolved. A dry powdered sample of 95% Rebaudioside A blend (RA95) corresponding to a final concentration of 60000 ppm (6%) was then added to the vial and the vial was capped and vortexed for 4 seconds. After vortexing, the aqueous buffered solution was observed for dissolution of the RA95. The RA95 had dissolved into solution and the aqueous buffered solution was clear. The RA95 blend added to the aqueous buffered solution with the dissolution enhancer compounds dissolved completely after vortexing. This experiment showed that the RA95 blend at a final steviol glycoside concentration of 60000 ppm (6%) was able to dissolve completely in the aqueous buffered solution containing the dissolution enhancer compound from *stevia* at a final concentration of 60000 ppm (6%).

TABLE 5

| Time (min) | Observation |
| --- | --- |
| 0 | Cloudy |
| 0.10 | Less cloudy |
| 0.15 | Less cloudy with some steviol glycoside crystals remaining |
| 0.20 | Completely clear |

Example 6

A 1:1 (wt) solution of the RM80 and the dissolution enhancer compound was prepared and co-dried to produce a dry 1:1 (wt) mixture. RM80 was added to a control vial. The 1:1 (wt) mixture of the RM80 and the dissolution enhancer compound was added to a test vial. Room temperature water was added to each vial. The room temperature water was added to the control vial in an amount to yield a 5% (wt) solution of the RM80. The room temperature water was added to the test vial in an amount to yield a solution of 5% (wt) RM80 and 5% (wt) SG dissolution enhancer. The vials were capped immediately after the water was added and each vial shaken by hand for about 10 seconds and observed immediately after shaking. The control vial showed that the RM80 did not dissolve. The test vial showed that the 1:1 (wt) mixture of the RM80 and the dissolution enhancer compound dissolved. The solutions were monitored over time. The solution of the test vial remained dissolved after 2 weeks of time. This experiment showed that the RM80 with dissolution enhancer compound was able to dissolve. The experiment also showed a high rate of instantaneous solubility of the RM80 with dissolution enhancer compound.

Example 7

Several vials were prepared to examine the effect of temperature on the dissolution of Reb M in water. For each experiment, a vial was prepared with an appropriate amount of steviol glycoside powder (RM80 or RM90). Dissolution enhancer was added to the vials as described in Table 6. Water was added to each vial to achieve the final concentrations described in Table 6. The vials were mixed by hand and placed in warm water baths at increasing temperatures. The minimum temperature required to dissolve the steviol glycosides is recorded in Table 6 as well as the time required at that temperature to reach complete dissolution.

TABLE 6

| Reb M Lot | SG concentration (ppm) | Dissolution enhancer concentration (ppm) | SE:SG Ratio | Temperature required (° C.) | Time for complete dissolution (minutes) |
| --- | --- | --- | --- | --- | --- |
| Lot #2 | 270 | 0 | — | 65 | 2 |
| Lot #2 | 270 | 270 | 1:1 | 20 | 2 |
| Lot #2 | 450 | 0 | — | 65 | 2 |
| Lot #2 | 450 | 300 | 2:3 | 20 | 2 |
| Lot #1 | 500 | 0 | — | 65 | 6 |
| Lot #1 | 500 | 250 | 1:2 | 20 | 4.5 |
| Lot #1 | 500 | 375 | 3:4 | 20 | 4.5 |
| Lot #2 | 600 | 0 | — | 65 | 2 |
| Lot #2 | 600 | 400 | 2:3 | 20 | 2 |
| Lot #2 | 700 | 0 | — | 65 | 2 |
| Lot #2 | 700 | 475 | 2:3 | 20 | 2 |
| Lot #1 | 2990 | 0 | — | 65 | 12 |
| Lot #1 | 2990 | 1500 | 1:2 | 40 | 10 |
| Lot #1 | 2990 | 2240 | 3:4 | 20 | 4 |

The invention claimed is:

1. A method for preparing a steviol glycoside solution, the method comprising:
    adding to an aqueous solution crystalline rebaudioside M; one or more dicaffeoylquinic acids or salts thereof; and one or more monocaffeoylquinic acids or salts thereof to form the steviol glycoside solution,
    wherein rebaudioside M is at least 70% by weight of total steviol glycosides in the steviol glycoside solution; and
    wherein dissolution of rebaudioside M at room temperature is faster than dissolution of rebaudioside M alone without the one or more dicaffeoylquinic acids or salts thereof and without the one or more monocaffeoylquinic acids or salts thereof, such that when the crystalline rebaudioside M; one or more dicaffeoylquinic acids or salts thereof; and one or more monocaffeoylquinic acids or salts thereof added to an aqueous solution to form a 3000 ppm steviol glycoside solution, the rebaudioside M is completely dissolved in less than 15 minutes.

2. The method of claim 1, wherein the ratio of total steviol glycosides to total of monocaffeoylquinic acids or salts and dicaffeoylquinic acids and salts is between 1:0.3 to 1:3 in the steviol glycoside solution.

3. The method of claim 1, wherein the ratio of total steviol glycosides to total of monocaffeoylquinic acids or salts and dicaffeoylquinic acids and salts is between 1:1 to 1:3 in the steviol glycoside solution.

4. The method of claim 1, wherein the one or more dicaffeoylquinic acids or salts thereof comprise one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

5. The method of claim 1, wherein the one or more monocaffeoylquinic acids or salts thereof comprise one or more of 3-O-caffeoylquinic acid, 4-O-caffeoylquinic acid, 5-O-caffeoylquinic acid, and salts thereof.

6. The method of claim 1, wherein the total steviol glycosides comprises rebaudioside D.

7. The method of claim 1, wherein the total steviol glycosides comprises rebaudioside A.

8. The method of claim 1, wherein the total steviol glycosides, the one or more dicaffeoylquinic acid or salt thereof and the one or more monocaffeoylquinic acid or salt thereof are co-dried prior to addition to the aqueous solution.

9. The method of claim 1, wherein the one or more dicaffeoylquinic acids or salts thereof and the one or more monocaffeoylquinic acids or salts thereof are prepared from a botanical source.

10. The method of claim 9, wherein the botanical source is yerba mate.

11. The method of claim 9, wherein the botanical source is *stevia*.

12. The method of claim 1, wherein the total of monocaffeoylquinic acids or salts and dicaffeoylquinic acids and salts comprises at least 15% dicaffeoylquinic acids and salts thereof.

13. The method of claim 1, wherein at least one of 3-O-feruloylquinic acid, 4-O-feruloylquinic acid, 5-O-feruloylquinic acid, 3,4-diferuloylquinic acid, 3,5-diferuloylquinic acid, or 4,5-diferuloylquinic acid is also added to the aqueous solution.

14. The method of claim 1, wherein the aqueous solution comprises less than 1% C1-C4 alcohols.

15. The method of claim 1, wherein the aqueous solution is substantially free of C1-C4 alcohols.

16. The method of claim 1, wherein the total steviol glycosides, dicaffeoylquinic acids or salts thereof, and monocaffeoylquinic acids or salts thereof are added to the aqueous solution at a temperature less than 30° C., the total steviol glycoside concentration is at least 5 wt % in the steviol glycoside solution, and the rebaudioside M completely dissolves in less than 10 seconds.

17. The method of claim 1, wherein the final concentration of steviol glycoside in the steviol glycoside solution is between 3000 ppm and 60000 ppm.

18. The method of claim 1, wherein total steviol glycoside in the steviol glycoside solution comprises less than 1 wt % of rebaudioside A.

19. The method of claim 1, wherein total steviol glycoside in the steviol glycoside solution comprises less than 1 wt % rebaudioside A, at least 80 wt % rebaudioside M, and between 10 wt % and 20 wt % rebaudioside D.

* * * * *